United States Patent
McDaniel

(10) Patent No.: US 6,738,664 B1
(45) Date of Patent: May 18, 2004

(54) METHOD OF AND APPARATUS FOR ATRIAL AND VENTRICULAR DEFIBRILLATION OR CARDIOVERSION WITH AN ELECTRICAL WAVEFORM OPTIMIZED IN THE FREQUENCY DOMAIN

(75) Inventor: Wayne C. McDaniel, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 590 days.

(21) Appl. No.: 09/669,497

(22) Filed: Sep. 25, 2000

Related U.S. Application Data

(60) Provisional application No. 60/155,847, filed on Sep. 24, 1999.

(51) Int. Cl.[7] .................................................. A61N 1/39
(52) U.S. Cl. .............................................. 607/5; 607/72
(58) Field of Search ................................. 607/4–5, 7–8, 607/68, 72; 600/547

(56) References Cited

U.S. PATENT DOCUMENTS

| | | | |
|---|---|---|---|
| 4,637,397 A | 1/1987 | Jones et al. ............. | 128/419 D |
| 4,821,723 A | 4/1989 | Baker, Jr. et al. ........ | 128/419 D |
| 5,246,000 A | * 9/1993 | Ellis et al. ..................... | 607/27 |
| 5,468,254 A | 11/1995 | Hahn et al. | |
| 5,593,427 A | 1/1997 | Gliner et al. ................... | 607/7 |
| 5,601,612 A | 2/1997 | Gliner et al. ................... | 607/7 |
| 5,620,470 A | 4/1997 | Gliner et al. ................... | 607/7 |
| 5,769,872 A | 6/1998 | Lopin et al. .................... | 607/5 |
| 5,797,968 A | 8/1998 | Lopin et al. .................... | 607/5 |
| 5,803,927 A | 9/1998 | Cameron et al. .............. | 607/5 |

FOREIGN PATENT DOCUMENTS

| WO | 97/38754 | 10/1997 |
|---|---|---|

OTHER PUBLICATIONS

Achleitner, U. et al.; "Waveforms Of External Defibrillators: Analysis And Energy Contribution"; *Elseiver Science Ireland Ltd.; Resuscitation 41*; pp. 193–200, 1999.

Ammer, R. et al.; "Pain Threshold For Low Energy Intracardiac Cardioversion Of Atrial Fibrillation With Low Or No Sedation"; *PACE*; vol. 20; pp. 230–236; 1997.

Bardy, G.H. et al.; "Truncated Biphasic Pulses For Transthoracic Defibrillation"; *Circulation*; vol. 91; No. 6; pp. 1768–1774; 1995.

Brady, G.H. et al.; "Multicenter Comparison Of Truncated Biphasic Shocks And Standard Damped Sine Wave Monophasic Shocks For Transthoracic Ventricular Defibrillation"; *Circulation*; vol. 94; No. 10; pp. 2507–2514, 1996.

Chapman, P.D. et al.; "Comparision Of Monophasic With Single And Dual Capacitor Biphasic Waveforms For Nonthoracotomy Canine Internal Defibrillation"; *JACC*; vol. 14; No. 1; pp. 242–245, 1989.

Cleland, B.G; "A Conceptual Basis For Defibrillation Waveforms"; *PACE*; vol. 19; pp. 1186–1195; 1996.

Cooper, R.A.S. et al.; "Internal Cardioversion Of Atrial Fibrillation In Sheep"; *Circulation*; vol. 87; No. 5; pp. 1673–1686; 1993.

(List continued on next page.)

*Primary Examiner*—Kennedy Schaetzle
*Assistant Examiner*—Kristen Droesch
(74) *Attorney, Agent, or Firm*—Senniger, Powers, Leavitt & Roedel

(57) ABSTRACT

An apparatus having a discharging energy source, two electrodes adapted to make electrical contact with a patient, a connecting mechanism forming an electrical circuit between the energy source and the electrodes and a controller operating the connecting mechanism. The apparatus delivers electrical energy from the energy source to the electrodes having a waveform optimized in the frequency domain to have a dominant frequency in a preset range.

44 Claims, 22 Drawing Sheets

OTHER PUBLICATIONS

Dixon, E.G. et al.; "Improved Defibrillation Thresholds With Large Contoured Epicardial Electrodes And Biphasic Waveforms"; *Circulation*; vol. 76; No. 5; pp. 1176–1184; 1987.

Fishler, M.G.; "Theoretical Predictions Of The Optimal Monophasic And Biphasic Defibrillation Waveshapes"; IEEE *Transactions On Biomedical Engineering*; vol. 47; No. 1; pp. 59–67; 2000.

Greene, H.L. et al.; "Comparison Of Monophasic And Biphasic Defibrillating Pulse Waveforms For Transthoracic Cardioversion"; *The American Journal of Cardiology*; vol. 75; pp. 1135–1139; 1995.

Harbinson, M.T. et al.; "Rounded Biphasic Waveform Reduces Energy Requirements For Transvenous Catheter Cardioversion Of Atrial Fibrillation And Flutter"; *PACE*; vol. 20; pp. 226–229; 1997.

Heavens, J.P. et al.; "Effects Of Transthoracic Impedance And Peak Current Flow On Defibrillation Success In A Prehospital Setting"; *Annals Of Emergency Medicine*; pp. 191–199; 1998.

Irnich, W.; "The Fundamental Law Of Electrostimulation And Its Application To Defibrillation"; PACE; vol. 13; pp. 1433–1447; 1990.

Keane, D. et al.; "Comparision Of Biphasic And Monophasic Waveforms In Epicardial Atrial Defibrillation"; *JACC*; vol. 24; No. 1; pp. 171–176; 1994.

Keener, J.P. et al.; "The Biphasic Mystery: Why A Biphasic Shock Is More Effective Than A Monophasic Shock For Defibrillation"; *J. Theor. Biol.*; pp. 1–17; 1999.

Kroll, M.W.; "A Minimal Model Of The Single Capacitor Biphasic Defibrillation Waveform"; *PACE*; vol. 17; pp. 1782–1792; 1994.

Kroll, M.W. et al.; "Automated External Defibrillators: Design Considerations"; *New Horizons*; vol. 5; No. 2; pp. 128–136; 1997.

Lin, J.H. et al.; "Comparison Of Defibrillation Efficacy Using Biphasic Waveforms Delivered From Various Capacitances/Pulse Widths"; *PACE*; vol. 20; pp. 158–162; 1997.

Mittal, S. et al.; "Comparison Of A Novel Rectilinear Biphasic Waveform With A Damped Sine Wave Monophasic Waveform For Transthoracic Ventricular Defibrillation"; *Journal of American College of Cardiology*; vol. 34; No. 5; pp. 1595–1601; 1999.

Murgatroyd, F.D. et al.; "Efficacy And Tolerability Of Transvenous Low Energy Cardioversion Of Paroxysmal Atrial Fibrillation In Humans"; *JACC*; vol. 26; No. 6; pp. 1347–1353; 1995.

Negovsky, V.A.; "The Nature Of Electric Defibrillation Of The Heart"; *Resuscitation*; No. 2; pp. 255–259; 1973.

Poole, J.E. et al.; "Low–Energy Impedance–Compensating Biphasic Waveforms Terminate Ventricular Fibrillation At High Rates In Victims Of Out–Of–Hospital Cardiac Arrest"; *Journal of Cardiovascular Electrophysiology*; vol. 8; No. 12; pp. 1373–1385; 1997.

Schuder, J.C. et al.; "Transthoracic Ventricular Defibrillation In The Dog With Truncated And Untruncated Exponential Stimuli"; *IEEE Transactions On Bio–Medical Engineering*; vol. BME-18; No. 6; pp. 410–415; 1971.

Schuder, J.C. et al.; "Transthoracic Ventricular Defibrillation IN The 100 kg Calf With Symmetrical One–Cycle Bidirectional Rectangular Wave Stimuli"; *IEEE Transactions on Biomedical Engineering*; vol. BME-30; No. 7; pp. 415–422; 1983.

Schuder, J.C. et al.; "Defibrillation In The Calf With Bidirectional Trapezoidal Wave Shocks Applied Via Chronically Implanted Epicardial Electrodes"; *Trans Am Soc Artif Intern Organs*; vol. XXVII; pp. 467–470; 1981.

Schuder, J.C. et al.; "Trans Thoracic Defibrillation Of 100 kg Calves With Bidirectional Truncated Exponential Shocks"; *Trans Am Soc Artif Intern Organs*; vol. XXX; pp. 520–525; 1984.

Schuder, J.C. et al.; "Defibrillation Of 100 kg Calves With Asymmetrical Bidirectional Rectangular Pulses"; *Reprinted from Cardiovascular Research*; vol. XVIII; No. 7; pp. 419–426; 1984.

Schuder, J.C. et al.; "Comparison Of Effectiveness Of Relay–Switched, One–Cycle Quasisinusoidal Waveform With Critically Damped Sinusoid Waveform In Transthoracic Defibrillation Of 100–Kilogram Calves"; *Medical Instrumentation*; vol. 11; No. 6; pp. 281–285; 1988.

Schuder, J.C. et al.; "Relationship Between Efficacy Of Defibrillation Shocks And Frequency Characteristics Of Shock Waveforms"; *Journal of Cardiovascular Electrophysiology*; vol. 9; No. 10; pp. 1043–1054; 1998.

Schwartzman, D. et al.; "Serial Defibrillation Lead Impedance In Patients With Epicardial And Nonthoracotomy Lead Systems"; *Journal of Cardiovascular Electrophysiology*; vol. 7; No. 8; pp. 697–703; 1996.

Sweeney, R.J. et al.; "Defibrillation Using A High–Frequency Series Of Monophasic Rectangular Pulses: Observations and Model Predictions"; *Journal of Cardiovascular Electrophysiology*; vol. 7; No. 2; pp. 134–143; 1996.

Swerdlow, C.D. et al.; "Charge–Burping Theory Correctly Predicts Optimal Ratios Of Phase Duration For Biphasic Defibrillation Waveforms"; *Circulation*; vol. 94; No. 9; pp. 2278–2284; 1996.

Swerdlow, C.D. et al.; "Application Of Models Of Defibrillation To Human Defibrillation Data"; *Circulation*; vol. 96; No. 9; pp. 2813–2822; 1997.

Tomassoni, G. et al.; "Testing Different Biphasic Waveforms And Capacitances: Effect On Atrial Defibrillation Threshold And Pain Perception"; *JACC*; vol. 28; No. 3; pp. 695–699; 1996.

Walcott, G.P. et al.; "Choosing The Optimal Monophasic And Biphasic Waveforms For Ventricular Defibrillation"; *Journal of Cardiovascular Electrophysiology*; vol. 6; No. 9; pp. 737–750; 1995.

White, R.D.; "Early Out–Of–Hospital Experience With An Impedance–Compensating Low–Energy Biphasic Waveform Automatic External Defibrillator"; *Journal of Interventional Cardiac Electrophysiology*; pp. 203–208; 1997.

Yamanouchi, Y. et al.; "Optimal Small–Capacitor Biphasic Waveform For External Defibrillation; Influence of Phase–1 Tilt And Phase–2 Voltage"; *Circulation*; pp. 2487–2493; 1998.

Zipes, D.P. et al.; "Termination Of Ventricular Fibrillation In Dogs By Depolarizing A Critical Amount Of Myocardium"; *The American Journal of Cardiology*; vol. 36; pp. 37–44; 1975.

Angeion Corporation; "ARD Operations Manual," 1998.

McDaniel W.C.; Abstract of "Multiphasic Waveforms Require Less Peak Current For Atrial And Ventricular Defibrillation Than Biphasic Waveforms"; *Europace Supplements*; vol. 1; No. 122PW/7; 2000, p. D155.

McDaniel, W.C.; Abstract of "Multiphasic Waveforms Are More Effective for External Defibrillation Than Biphasic Waveforms," Eurospace Supplements, vol. 1, Jul. 2000, p. D272, No. 184P/4.

McDaniel, W.C.; Abstract of "Multiphasic Sinusoidal Waveforms Improve Defibrillation Efficacy Over Biphasic Sinusoidal Waveforms," PACE, vol. 23, Part II, Apr. 2000, p. 707, No. 620.

McDaniel, W.C.; Abstract of "Multiphasic Truncated Exponential Waveforms Improve Defibrillation Efficacy Over Biphasic Truncated Exponential Waveforms," PACE, vol. 23, Apr. 2000, Part II, p. 697, No. 578.

McDaniel, W.C.; Abstract of "Multiphasic Truncated Exponential Waveforms Reduce Peak Current Required for Atrial Defibrillation Compared to Biphasic Waveforms," PACE, vol. 23, Apr. 2000, Part II, p. 678, No. 501.

McDaniel, W.C.; Abstract of "Multiphasic Waveforms Improve External Defibrillation Efficacy Over Biphasic Waveforms," PACE, vol. 23, Apr. 2000, Part II, p. 632, No. 320.

McDaniel, W.C.; Abstract of "External Ventricular Defibrillation With Sinusoidal Waveforms Of A Varying Frequency"; *NASPE* Abstracts; Part II; No. 452; 1996, p. 679.

McDaniel, W.C.; Abstract of "Ventricular Defibrillation With Transvenous Electrodes And Sinusoidal Waveforms Of Varying Frequency"; Circulation; vol. 94; No. 8; No. 2558; Supp. 1, pp. 1–438.

Sulke, N. et al.; Abstract of "A Prospective Evaluation Of Recurrent Atrial Endocardial Defibrillation IN Patients With Refractory Chronic Atrial Flutter And Fibrillation"; *NAPSE Abstracts*; Part II; No. 235; 1996, p. 624.

Gonzalez, X. et al., Abstract of "Waveforms to Reduce Peak Voltages for Internal Atrial Defibrillation," PACE, vol. 19, Apr. 1996, Part II, p. 696, No. 521.

Reilly, P., "Cardiac Sensitivity to Electrical Stimulation," Electrical Stimulation and Electropathology, Chapter 6, Cambridge University Press, pp. 180–230 (est. 1989).

Guse, P., et al., "Defibrillation Electrode Configurations Developed from Cardiac Mapping that Combine Biphasic Shocks with Sequential Timing," American Heart Journal, 1992, vol. 124, No. 6, pp. 1491–1500.

Cooper, R., et al., "Internal Atrial Defibrillation in Humans: Improved Efficacy of Biphasic Waveforms and the Importance of Phase Duration," Circulation, vol. 95, No. 6, 1997, pp. 1487–1496.

Blanchard, et al., "Mechanisms of Electrical Defibrillation: Impact on new Experimental Defibrillator Waveforms," American Heart Journal, 1994, vol. 127, No. 4, Part 2, pp. 970–977.

Kavanagh, K., et al., "Monophasic Versus Biphasic Cardiac Stimulation: Mechanism of Decreased Energy Requirements," PACE, vol. 13, Oct. 1990, pp. 1268–1276.

Yamanouchi, Y., et al., "Large Change in Voltage at Phase Reversal Improves Biphasic Defibrillation Thresholds," Circulation, vol. 94, No. 7, Oct. 1, 1996, pp. 1768–1773.

Weirich, et al., "Factors Determining the Susceptibility of the Isolated Guinea Pig Heart to Ventricular Fibrillation Induced by Sinsusoidal Alternating Current at Frequencies from 1 to 1000 Hz," Basic Research in Cardiology, vol. 78, 1983, pp. 604–616.

Kugelberg, J., "Electrical Induction of Ventricular Fibrillation in the Human Heart," Scand. J. Thor. Cardiovasc. Surg., vol. 10, 1976, pp. 237–240.

Witzel D., et al., "The Influence of Cycle Frequency on the Effectiveness of Electrical Defibrillation of the Canine Ventricles," Cardiovascular Research Center Bulletin, 1967, vol. 5, No. 4., pp. 112–118.

Cooper, R., "Internal Cardioversion of Atrial Fibrillation: Marked Reduction in Defibrillation Threshold with Dual Current Pathways," Circulation, vol. 96, No., 8, Oct. 21, 1997, pp. 2693–2700.

Boriani, G., et al., "Transvenous Internal Cardioversion for Atrial Fibrillation: A Randomized Study on Defibrillation Threshold and Tolerability of Asymmetrical Compared with Symmetrical Shocks," International Journal of Cardiology, vol. 71, 1999, pp. 63–69.

Liu, S., et al., "The Effects of Electrical Stimulation at Different Frequencies on Perception and Pain in Human Volunteers: Epidural Versus Intravenous Administration of Fentanyl," Anesth Analg., vol. 82, 1996, pp. 98–102.

Lok, N., et al., "Clinical Shock Tolerability and Effect of Different Right Atrial Electrode Locations on Efficacy of Low Energy Human Transvenous Atrial Defibrillation Using an Implantable Lead System," JACC, vol. 30, No. 5, Nov. 1, 1997, pp. 1324–1330.

Schuder, J., et al., "Transthoracic Ventricular Defibrillation with Square–wave Stimuli," Circulation Research, vol. XV, Sep. 1964, pp. 258–264.

Geddes, L., et al., "Evolution of the Optimum Bidirectional (±Biphasic) Wave for Defibrillation," Biomedical Instrumentation & Technology, Jan./Feb. 2000, pp. 39–54.

Yamanouchi, Y., et al., "Fully Discharging Phases: A New Approach to Biphasic Waveforms for External Defibrillation," Circulation, Aug. 24, 1999, pp. 826–831.

White, J., et al., "Predicting the Relative Efficacy of Shock Waveforms for Transthoracic Defibrillation in Dogs," Annals of Emergency Medicine, vol. 34, No. 3, Sep. 1999, pp. 309–320.

Beck, C., et al., "Ventricular Fibrillation of Long Duration Abolished by Electric Shock," Council on Physical Medicine, vol. 135, No. 15., Dec. 13, 1947, pp. 985–986.

Lown, B., et al., "Comparison of Alternating Current with Direct Current Electroshock Across the Closed Chest," American Journal of Cardiology, Aug. 1962, pp. 223–233.

Gullett, J., et al., "Optimum Duration of 60–Hz Current for Direct Ventricular Defibrillation in the Dog," Cardiovascular Research Center Bulletin, vol. 6, No. 3, Jan.–Mar., 1968, pp. 117–123.

Tacker, W., et al., "Defibrillation of the Dog Ventricles Using Single and Multiple Half–Sinusoidal Current Pulses," Cardiovascular Research Center Bulletin, vol. 10, No. 2, Oct.–Dec., 1971, pp. 57–067.

Geddes, L., et al., "Electrical Ventricular Defibrillation," Cardiovascular Research Center Bulletin, vol. 10, No. 1, Jul.–Sep., 1971, pp. 3–41.

McDaniel, W., "Potential Role of Frequency–Domain Representation in Selection of Optimal Defibrillatory Shock," IEEE, 0–7803–2050–6/94, published Mar. 11, 1994, pp. 19–20, Columbia, Missouri.

International Search Report, PCT/US00/26238, Feb. 22, 2001, 5 pages.

* cited by examiner

39 Ohms, 143 J

85 Ohms, 143 J

138 Ohms, 143 J

39 Ohms, 153 J

85 Ohms, 143 J

138 Ohms, 126 J

39 Ohms, 150 J

85 Ohms, 143 J

138 Ohms, 144 J

ONE-HALF CYCLE-25 Hz

ONE-CYCLE-50 Hz

ONE AND ONE-HALF CYCLE-75 Hz

TWO CYCLE-100 Hz

TWO AND ONE-HALF CYCLE-125 Hz

THREE CYCLE-150 Hz

THREE AND ONE-HALF CYCLE-175 Hz

FOUR CYCLE-200 Hz

FIVE CYCLE-250 Hz

SIX CYCLE-300 Hz

ONE-HALF CYCLE-12.5 Hz

ONE CYCLE-25 Hz

ONE AND ONE-HALF CYCLE-37.5 Hz

TWO CYCLE-50 Hz

TWO AND ONE-HALF CYCLE-62.5 Hz

THREE CYCLE-75 Hz

THREE AND ONE-HALF CYCLE-87.5 Hz

FOUR CYCLE-100 Hz

EDMARK

39 Ohms

BTE (HEARTSTREAM)

39 Ohms

QUADRIPHASIC

39 Ohms

EDMARK

85 Ohms

BTE (HEARTSTREAM)

85 Ohms

QUADRIPHASIC

85 Ohms

EDMARK

138 Ohms

BTE (HEARTSTREAM)

138 Ohms

QUADRIPHASIC

138 Ohms

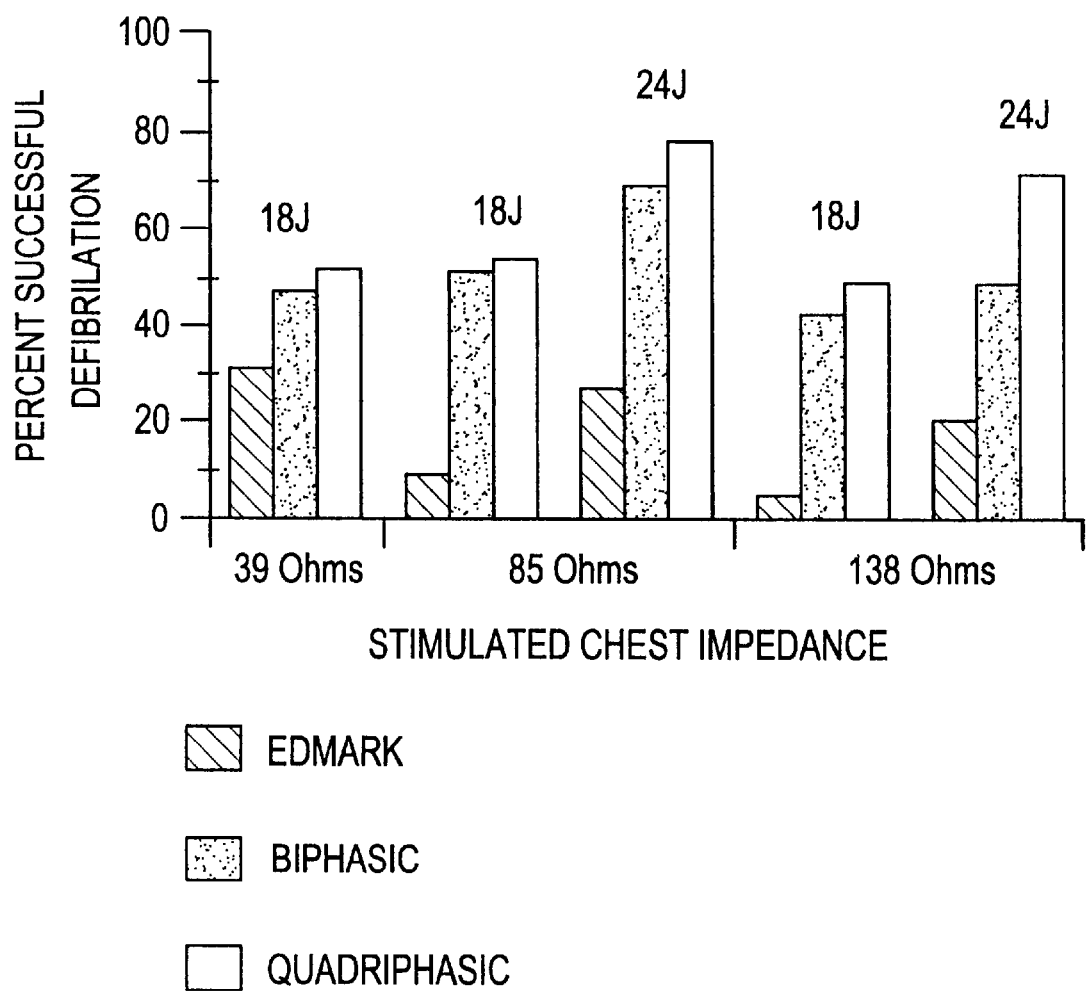

TIME (msec)

TIME (msec)

TIME (msec)

TIME (msec)

TIME (msec)

TIME (msec)

TIME (msec)

TIME (msec)

METHOD OF AND APPARATUS FOR ATRIAL AND VENTRICULAR DEFIBRILLATION OR CARDIOVERSION WITH AN ELECTRICAL WAVEFORM OPTIMIZED IN THE FREQUENCY DOMAIN

This application claims benefit of provisional app. No. 60/155,847 filed Sep. 24, 1999.

BACKGROUND OF THE INVENTION

When the first animal and human defibrillations were reported with both internal and external electrodes, the electrical waveform utilized was a 60 cycles/second (Hz) sinusoidal waveform. This electrical shock was obtained by modifying the available voltage, typically 110 V(rms), such as by stepping up or stepping down the voltage. Durations were approximately in the range of 100 to 150 milliseconds (msec). Disadvantages to this methodology included: the defibrillator was very large and not easily portable; the defibrillator had to be plugged into the wall and, therefore, the patients had to be in the hospital; and there was a large current draw during the shock, which blew fuses and dimmed other lights on the circuit.

In the 1960's Edmark and Lown independently developed new waveforms for defibrillation which are called RLC waveforms. These waveforms are generated with a circuit containing a capacitor (C), an inductor (L), and a resistance (R). Advantages to the use of these waveforms included: the defibrillator was small and portable; it could be powered by a battery and used out of the hospital; and it did not draw huge amounts of current. These waveforms quickly became the standard for transthoracic defibrillation, and are still the industry standard for transthoracic defibrillation today.

When the implantable cardioverter/defibrillator (ICD) was developed in the 1970s [Schuder et al, Trans ASAIO, 16:207–12], the waveform of choice was the monophasic truncated exponential (MTE) as this waveform could be generated without an inductor (which could not be miniaturized for implantable devices). The MTE waveform was pioneered by the laboratory at University of Missouri [Gold et al, Circ 56:745–50, 1977] and was incorporated into most ICDs for clinical use for the first decade of their use.

In a series of papers in the early 1980s, the laboratory at the University of Missouri ("MU Lab") pioneered a new class of waveforms for electrical ventricular defibrillation, called bidirectional or biphasic waveforms. The MU Lab demonstrated that if one were to reverse the polarity of an MTE waveform for the second half of the duration to yield a biphasic truncated exponential waveform (BTE), that one could dramatically improve the efficacy of defibrillation. The MU Lab studies covered the cases where the second phase amplitude was equal to the first phase amplitude and constant; where the second phase amplitude was smaller than the first phase amplitude and constant; and where the first and second phase amplitudes were allowed to decay exponentially and the second phase amplitude was either smaller than or equal to the first phase amplitude. Some of these waveforms studied were the first use of single capacitor waveforms (waveforms that could be generated by switching the polarity of a single capacitor) for defibrillation. These early studies utilized both internal and external electrodes.

The early studies from the MU lab arbitrarily set the first phase duration equal to the second phase duration. In 1987, Dixon et al published a paper, which found that if the first phase was longer than the second phase, that one could improve the efficacy of defibrillation over the case where the second phase duration was longer than the first phase duration [Dixon et al, Circ 76:1176–84]. The company that sponsored this research (Intermedics, Inc.) subsequently received U.S. Pat. No. 4,821,723 relating to this variation of the biphasic waveform. Biphasic truncated exponential (BTE) waveforms are now the industry standard for ICDs and also for implantable atrial defibrillators (IADs).

Several theories have been put forward, in an effort to understand why biphasic waveforms are generally more effective for electrical defibrillation than are monophasic waveforms. Understanding the mechanism of biphasic waveform superiority will possibly allow the design of even better waveforms for the next generation of defibrillators. The dominant theory in the field is currently a group of theories which can collectively be called RC circuit model theories. These theories have the common feature of modeling the response of the heart to a defibrillation shock, as the response of a resistor-capacitor (RC) circuit to that same shock. These theories also share the view that defibrillation efficacy is determined by the maximal capacitor voltage (model response) and the final capacitor voltage (model response). Taken as a group, these theories have led investigators to postulate optimal BTE waveforms for both internal and external defibrillation. As an example, a 1997 PCT publication "External defibrillator having low capacitance and small time constant" [WO 97/38754] relates to a BTE according to one version of the RC circuit model theory. Other theories of defibrillation have similarly led to different optimal waveform designs.

There are three different phenomena where electrotherapy shocks such as these are useful. The three phenomena are ventricular defibrillation, atrial defibrillation, and cardioversion; which are the treatment by electrical shock of ventricular fibrillation, atrial fibrillation, and atrial and/or ventricular tachycardia. Each of these three phenomena can be accomplished with electrodes that are external to the body, or with electrodes that are implanted either permanently or temporarily in the body. The state of the art treatment for all six combinations of these conditions and electrodes is presently some variation of the biphasic waveform. Currently, the same device is typically used for both ventricular defibrillation and cardioversion. For example, CPI Guidant calls their internal defibrillator an Automatic Implantable Cardioverter Defibrillator, which implies a single device with two functions.

The efficacy of these cardioverter and/or defibrillator devices in practice, is determined by the electrical waveform generated, and by the way the device compensates for variations in the patients to which it is applied. Specifically, the electrical impedance varies from patient to patient, and over time within a patient. This variation is much larger in magnitude when external electrodes are used, than when internal electrodes are used. Consequently, compensation for this variation in impedance is more critical in external defibrillators than in implantable defibrillators. Some devices use a passive impedance compensation strategy, whereby changes in impedance cause waveform changes without active intervention. Other devices actively compensate for impedance variation by measuring electrical parameters before or during the discharge such as capacitor voltage, patient impedance, or current flow; and modifying the electrical waveform based on these measurements.

For external ventricular defibrillation and cardioversion, the biphasic waveform of the Heartstream Inc.'s FORE-RUNNER® device is representative, and this device uses an active impedance compensation strategy. For an average impedance patient, it delivers a single capacitor BTE waveform with a 7 msec first phase and a 5 msec second phase, and uses a 100 microfarad capacitor. In response to variations in patient impedance, this device changes the durations of the two phases, the overall duration of the waveform, and the ratio of the durations of the two phases. The FIRST-SAVE® AED device made by SurVivaLink Corporation also delivers a biphasic waveform, and optimizes the waveform in terms of a charge-burping theory of defibrillation with active compensation for variations in impedance. Another alternative by Zoll Medical Corporation is the defibrillator waveform which has a saw-tooth (roughly constant current for all impedances) first phase, followed by a decaying exponential second phase. The biphasic waveform of the LIFEPAK® device by Physio-Control Corporation differs by using a longer time constant, and therefore a larger capacitance (about 300 microfarads). This device also uses an active impedance compensation strategy. External ventricular defibrillators on the market today deliver either a monophasic waveform (Edmark or truncated exponential) or some variation of the biphasic waveform, usually with the second phase shorter in duration and smaller in amplitude than the first phase. With applications such as the automatic external defibrillator (AED), it is very desirable to design a defibrillator that will work well with all impedance patients. In this application, simplicity of the circuitry is also an advantage, to reduce the cost of the devices, and promote more widespread availability.

For internal ventricular defibrillation and cardioversion, there are several companies that currently make devices, and most (if not all) of these devices deliver some version of a biphasic waveform. Many studies have been published, attempting to optimize the biphasic waveform for internal ventricular defibrillation. It is important to optimize the waveform for this application to avoid wasting energy, which will deplete the device battery prematurely. In addition, it is desirable to program the output of the implantable defibrillator to the lowest output level that will reliably defibrillate. This again avoids wasting battery life, as well as minimizing the detrimental effects of delivering too much energy to the heart. One patent that covers the biphasic waveform is the Baker et al patent, U.S. Pat. No. 4,821,723.

Another relevant patent is U.S. Pat. No. 4,637,397 on a triphasic waveform for defibrillation. In this patent, the figures show a small amplitude first phase, a larger amplitude second phase, and a very low amplitude final phase. This is in keeping with the inventor's theory that the first phase conditions the heart, the second phase defibrillates, and the final phase heals the heart. There have also been many other studies of a multitude of other waveforms, including many different multiphasic waveforms, most of which are delivered to two different pairs of electrodes in sequence. But none of these studies has resulted in a waveform that is clearly superior to the biphasic waveform for electrical ventricular defibrillation.

There have also been papers published of studies optimizing the biphasic waveform for atrial defibrillation. The first such paper (Cooper et al, Circulation 87:1673–86, 1993) found that the optimal BTE waveform was a single capacitor waveform that had a 3 msec first phase and a 3 msec second phase. Studies in patients, however reported that this waveform caused too much pain, and that a 6 msec plus 6 msec biphasic waveform allowed a reduction in peak current and also reduced the pain associated with the shock. However, this waveform is still associated with significant pain that has impeded its widespread clinical acceptance. Much of the current research in this area is concentrating on strategies to prevent AF, and pacing strategies to correct AF, without needing a defibrillation shock. Many physicians are reluctant to implant present atrial defibrillators, as the patients do not tolerate the pain associated with the shocks. A method that could electrically treat AF without pain would be a very welcome addition for therapy with implantable devices.

Another major application in need, is an external device connected to internal electrodes, for use (for example) in the intensive care unit with patients after heart surgery. As many as 40% of these patients will experience AF in about the first week after surgery. Not wanting to electrically shock these patients, they are typically kept in the hospital an extra day or two, until the AF resolves. After the first week, the increased incidence of AF disappears, and therefore an implanted unit is not needed. Another use of such a device could be in the electrophysiology laboratory, where a temporary catheter would be inserted to treat chronic atrial fibrillation. BTE waveforms have been tried in this application, but once again it was found that the pain associated with the shock was not acceptable to patients. A less painful, or painless therapy would be a very welcome addition to the treatment options for these patients.

From circuit theory, we know that if one increases the duration of a defibrillator shock, that the amplitude of the shock can be reduced and still deliver the same energy. Studies showed that biphasic waveforms with an overall duration of 12 msec were less painful for atrial defibrillation than those with an overall duration of 6 msec, and that they required less peak current. This led many to conclude that high peak currents were causing the pain of atrial defibrillation. Studies were performed to further increase the duration of the biphasic waveform, hoping to further reduce the peak current amplitude required for atrial defibrillation, and further reduce the associated pain. However, they reported, and recent studies confirmed, that the biphasic waveform for atrial defibrillation loses its efficacy as the duration is increased. This loss of efficacy is very pronounced with atrial defibrillation, as compared to the same waveforms used for ventricular defibrillation. Optimization of the biphasic waveform has not solved the problem of pain associated with an atrial defibrillation shock.

The effectiveness of an electrical defibrillation shock has been known for many years to be dependent on the shape of the electrical waveform. In other words, the manner in which current, or voltage, changes with time is critical to determining whether the electrical shock will successfully defibrillate the heart. This observation has naturally led many to conclude that the key to understanding the mechanism of electrical defibrillation would be found in studies of electrical waveforms in the time domain, wherein shock intensity is given as a function of time. Many of the theories of biphasic waveform superiority to monophasic waveforms postulate a two step process, wherein the first phase has one function and the second phase another. And the theory of the triphasic waveform of Jones also postulates a process that is sequential in time. However, these studies in the time domain have not solved some of the major challenges remaining in this field.

SUMMARY OF THE INVENTION

There exists, however, a parallel domain, the frequency domain, into which any electrical waveform from the time domain can be transformed. This transformation, which can be performed with the Fourier Transform, is a reversible transformation which means that all the information present in the time domain is also present in the frequency domain. Further, the inventor has found that there exists frequency ranges in the frequency domain representation, wherein the delivery of energy is associated with increased efficacy for electrical defibrillation, and that these optimal ranges may be different for the different applications of cardioversion and defibrillation shocks. It follows from this that there are frequency ranges in the frequency domain representation, wherein the delivery of energy is not associated with increased efficacy for electrical defibrillation. This invention optimizes defibrillation waveforms by maximizing the amount of energy delivered in the beneficial frequencies, and minimizing the amount of energy delivered in the other frequencies.

In addition, the full description of the Fourier transform requires information on the phase angle of the transform, and the inventor has found that defibrillation efficacy is also dependent on phase angle. Selecting a waveform so that the delivered energy is in optimal frequency ranges is one alternative condition of optimizing the waveforms in the frequency domain; selecting a waveform so that a dominant frequency of the waveform in the frequency domain is in a preselected range is another alternative condition of optimizing the waveforms in the frequency domain; and selecting the optimal phase angle of the transform of the waveform in the frequency domain is yet another alternative condition of optimizing the waveforms in the frequency domain.

The present invention improves the effectiveness of shocks used for electrical defibrillation or cardioversion of either the atria or ventricles, by maximizing the amount of energy delivered in an optimal frequency range and with the optimal phase angle. (As used herein, defibrillation includes cardioversion.) There are several advantages to the present invention over currently available technology, which are specific to the various applications of this invention.

Transthoracic Defibrillation—This invention can be applied to transthoracic defibrillation of humans, in which case the clinical device will be presented with widely varying patient impedance levels. Therefore, this invention is applied to design the waveform generated for a typical, or average impedance patient, and is also applied to design the impedance compensation strategy. The resultant waveform has the advantage of responding to different impedances by maximizing the amount of energy delivered in the optimal frequency range for ventricular defibrillation. The present invention in this application yields an electrical waveform for transthoracic ventricular defibrillation that has been demonstrated in animal studies to be more effective than the industry standard Edmark waveform at all simulated patient impedances. And this waveform has been demonstrated to be as effective as a state of the art biphasic waveform in simulated low and average impedance patients, and more effective than this prior art BTE waveform when the patient impedance is high. This waveform is also simpler to generate, and could lead to smaller, less expensive external defibrillators. When this invention is applied to external atrial defibrillation, the resultant optimal waveform may be different than the waveform for external ventricular defibrillation, as the optimal frequency range for atrial defibrillation appears in animal studies to be different than the optimal frequency range for ventricular defibrillation.

Internal Defibrillation—When applied to internal atrial or ventricular defibrillation, the present invention again has the advantage of optimizing the electrical waveform for each application, based on the optimal frequency ranges for that application. The present invention will also allow the generation of an electrical waveform for internal atrial defibrillation that is as effective as the prior art at varying patient impedances and that will defibrillate with appreciably less peak current than the prior art. This will likely translate into a waveform that causes less pain, when applied to humans in atrial fibrillation. In addition, this invention will allow the design of a waveform that is less effective at stimulating pain receptors, to cause less pain when applied to patients in atrial fibrillation. The present invention may also be applied to internal ventricular defibrillation, wherein by maximizing the amount of energy delivered in the optimal frequency range, one can improve the efficacy of the waveform across different patient impedances.

In one form, the invention comprises an apparatus for treating fibrillation or tachycardia comprising a discharging energy source, two electrodes adapted to make electrical contact with a patient, a connecting mechanism forming an electrical circuit between the energy source and the electrodes and a controller. The controller operates the connecting mechanism to deliver pulses of electrical energy from the energy source to the electrodes having a multiphasic waveform having three or more pulses optimized in the frequency domain.

In another form, the invention comprises a method of generating a waveform for treating fibrillation or tachycardia in a patient comprising discharging an energy source across electrodes in contact with the patient to deliver electrical energy from the energy source to the electrodes having a multiphasic waveform and optimizing the waveform in the frequency domain.

In yet another form, the invention comprises a discharging energy source, two electrodes adapted to make electrical contact with a patient, a connecting mechanism forming an electrical circuit between the energy source and the electrodes and a controller. The controller operates the connecting mechanism to deliver electrical energy from the energy source to the electrodes having a particular one of a plurality of waveforms, each of which is optimized in the frequency domain.

In yet another form, the invention comprises a signal for treating fibrillation or tachycardia comprising a multiphasic waveform containing three or more pulses optimized in the frequency domain.

Other objects and features will be in part apparent and in part pointed out hereinafter.

BRIEF DESCRIPTION OF THE DRAWINGS AND TABLES

Figure 5A:
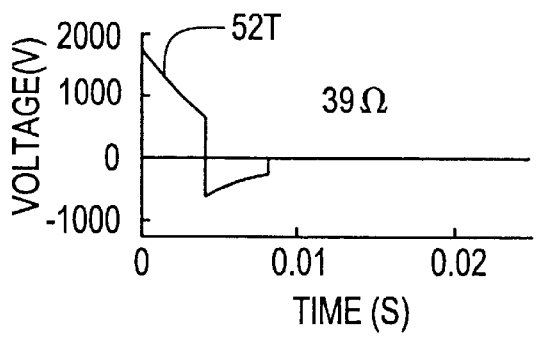
Figure 5D:
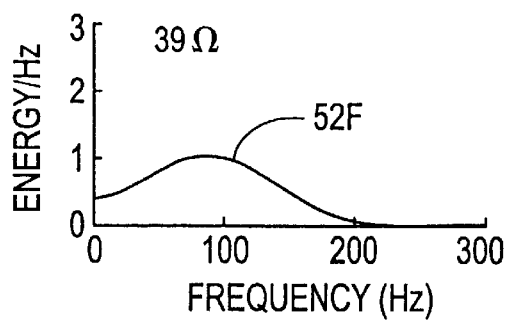
Figure 5B:
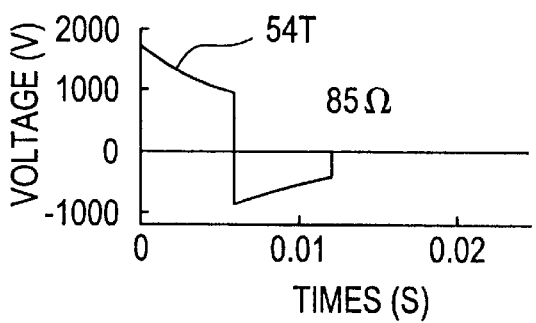
Figure 5E:
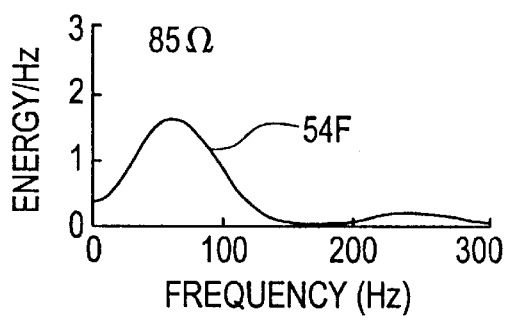
Figure 5C:
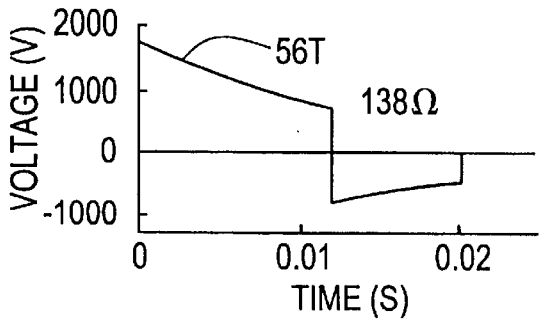

FIGS. 5A to 5C illustrate a variation of the automatic impedance compensation method chosen for Heartstream's FORERUNNER® device, showing a biphasic truncated exponential waveform, wherein the initial and final voltages of each pulse are constant with variations in impedance, only here with upper and lower limits placed on each phase duration, with the time domain representation for patient impedance values of 39, 85 and 138 ohms, respectively.

Figure 5F:
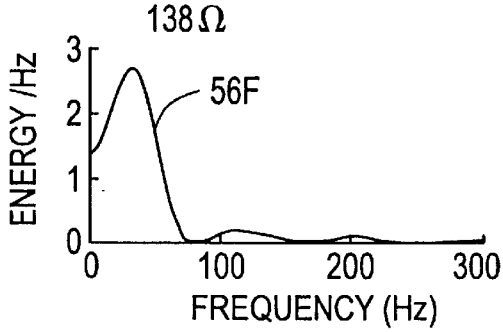

FIGS. 5D to 5F illustrate a variation of the automatic impedance compensation method chosen for Heartstream's FORERUNNER® device, showing a biphasic truncated exponential waveform, wherein the initial and final voltages of each pulse are constant with variations in impedance, only here with upper and lower limits placed on each phase duration, with the frequency domain representation for patient impedance values of 39, 85 and 138 ohms, respectively.

FIG. 5E illustrates a variation of the automatic impedance compensation method chosen for Heartstream's FORERUNNER® device, showing a biphasic truncated exponential waveform, wherein the initial and final voltages of each pulse are constant with variations in impedance, only here with upper and lower limits placed on each phase duration, with the frequency domain representation for patient a impedance value of 85 ohms.

FIG. 5F illustrates a variation of the automatic impedance compensation method chosen for Heartstream's FORERUNNER® device, showing a biphasic truncated exponential waveform, wherein the initial and final voltages of each pulse are constant with variations in impedance, only here with upper and lower limits placed on each phase duration, with the frequency domain representation for patient a impedance value of 138 ohms.

Figure 6A:
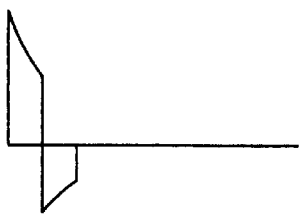
Figure 6B:
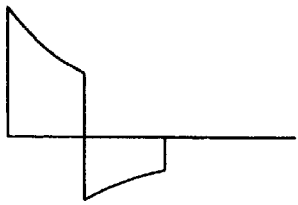
Figure 6C:
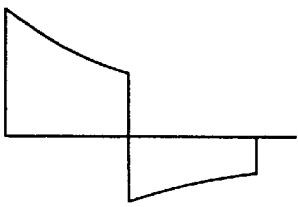

FIGS. 6A, 6B and 6C illustrate time domain waveforms for the manual method for patient impedance values of 39, 85 and 138 ohms, respectively.

Figure 6D:
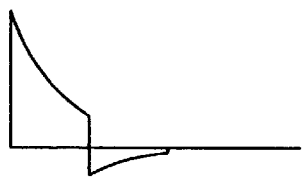
Figure 6E:
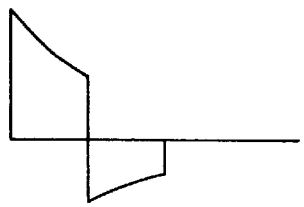
Figure 6F:
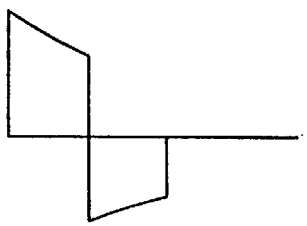

FIGS. 6D, 6E and 6F illustrate voltage based or automatic method for patient impedance values of 39, 85 and 138 ohms, respectively.

Figure 6G:
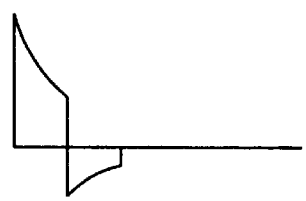
Figure 6H:
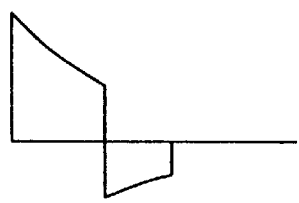
Figure 6I:
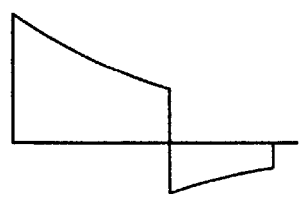
Figure 7A:
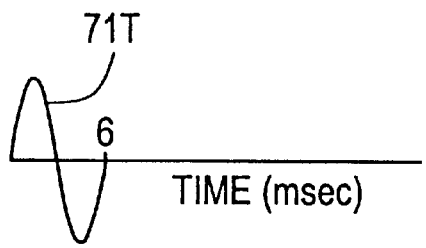
Figure 7E:
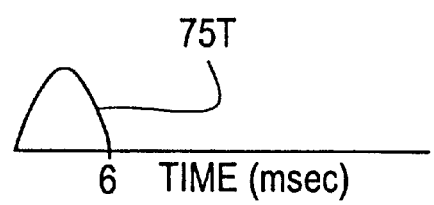
Figure 7B:
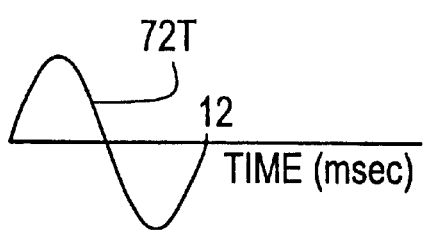
Figure 7F:
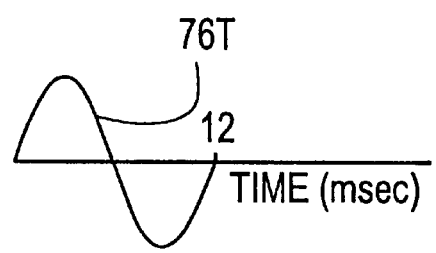
Figure 7C:
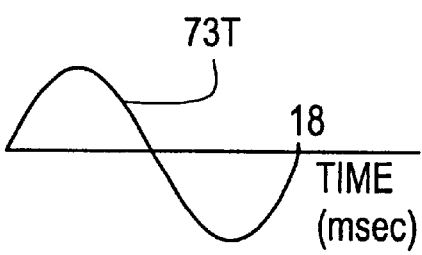
Figure 7G:
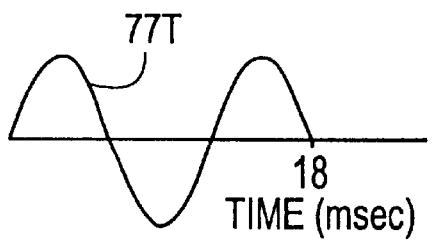
Figure 7D:
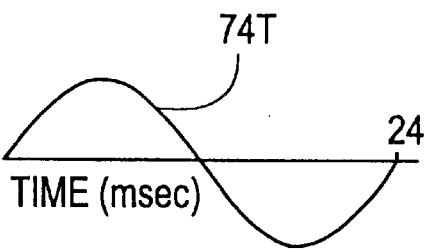
Figure 7H:
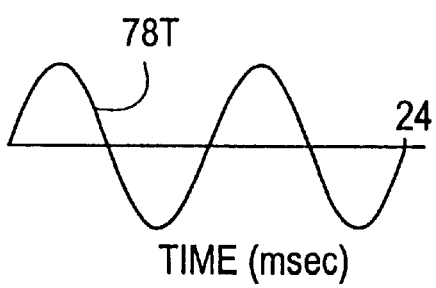

FIGS. 6G, 6H and 6I illustrate Heartstream's FORERUNNER® impedance compensation method for patient impedance values of 39, 85 and 138 Ohms, respectively.

FIGS. 7A, 7B, 7C and 7D show four biphasic sinusoidal waveforms studied in a canine model of ventricular defibrillation with transvenous electrodes and a pectoral can electrode with duration of 6, 12, 18, and 24 msec, respectively.

FIGS. 7E, 7F, 7G, and 7H show four multiphasic waveforms in which the individual phase duration is six msec, and total pulse durations are 6, 12, 18 and 24 msec, respectively.

Figure 8A:
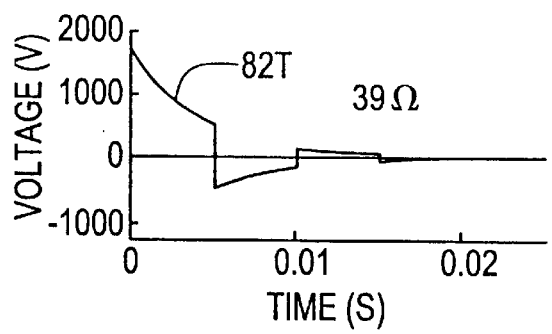
Figure 8D:
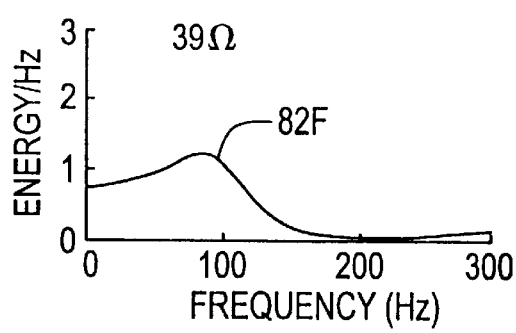
Figure 8B:
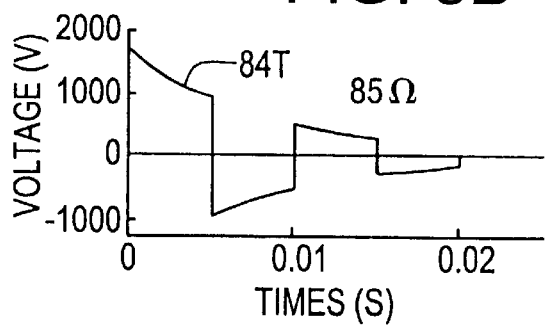
Figure 8E:
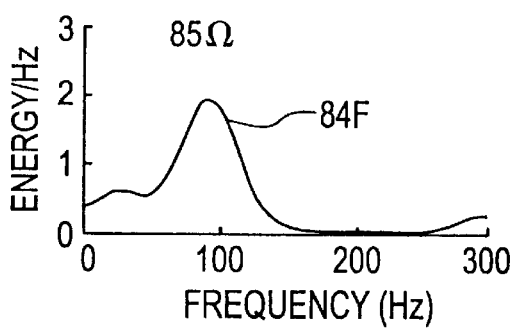
Figure 8C:
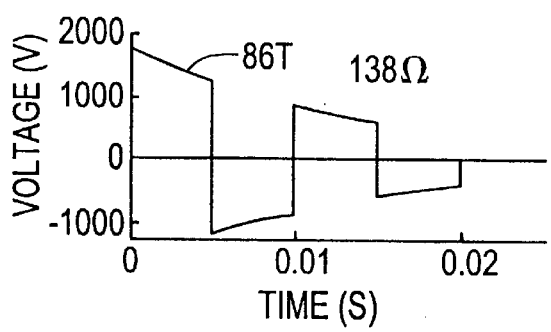

FIGS. 8A, 8B and 8C illustrate a multiphasic waveform showing the time domain representation for patient impedance values of 39, 85 and 138 Ohms, respectively.

Figure 8F:
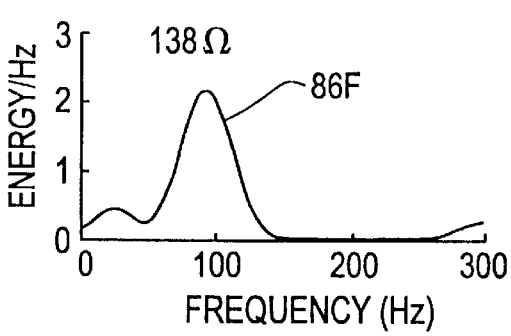

FIGS. 8D, 8E and 8F illustrate a multiphasic waveform showing the frequency domain representation for patient impedance values of 39, 85 and 138 Ohms, respectively. This demonstrates a first impedance compensation method wherein individual and total pulse durations are kept constant (and equal) and the frequency of stimulation is kept constant across the range of impedance variation, assuming a 100 $\mu f$ capacitor.

Figure 9A:
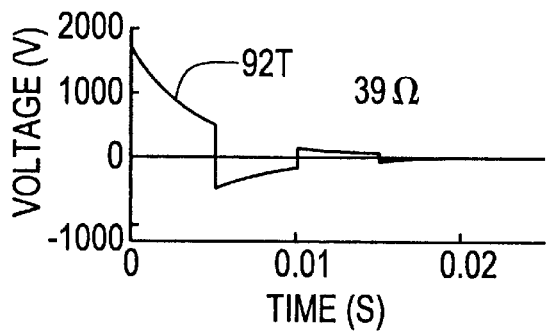
Figure 9D:
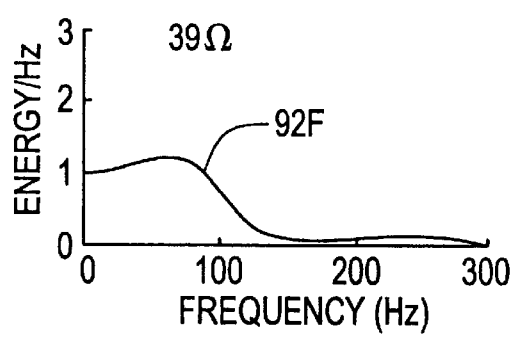
Figure 9B:
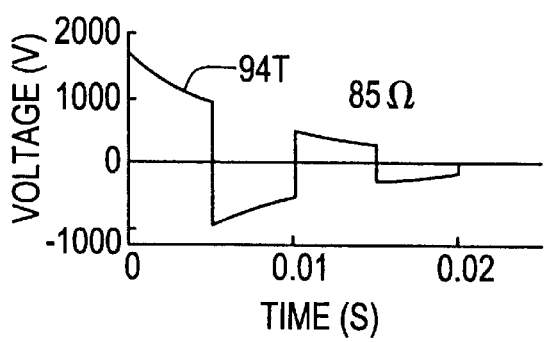
Figure 9E:
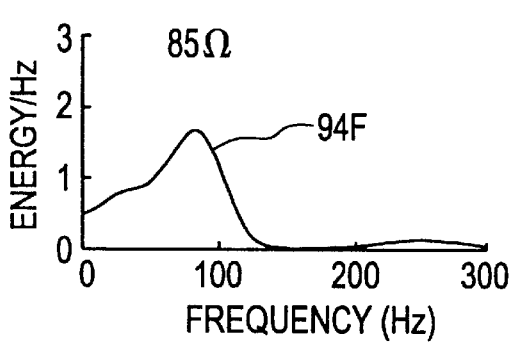
Figure 9C:
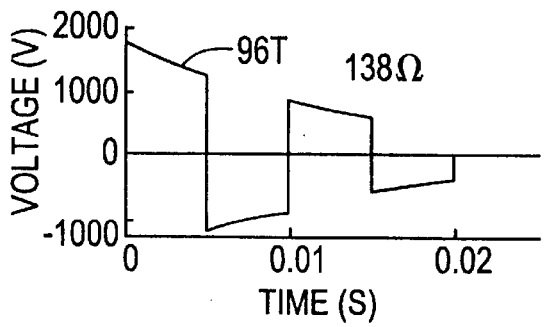

FIGS. 9A, 9B and 9C illustrates a multiphasic waveform showing the time domain representation in the left column and showing the frequency domain representation for patient impedance values of 39, 85 and 138 Ohms, respectively.

Figure 9F:
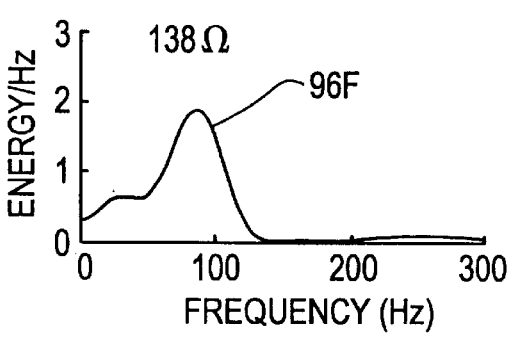
Figure 10A:
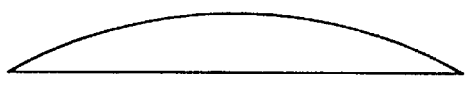
Figure 10B:
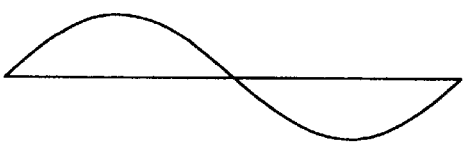
Figure 10C:
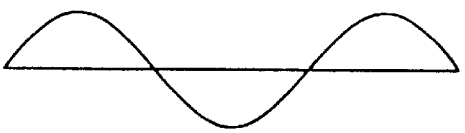
Figure 10D:
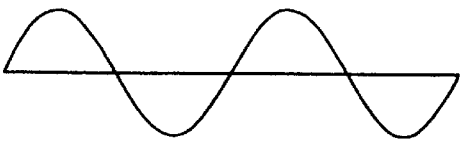
Figure 10E:
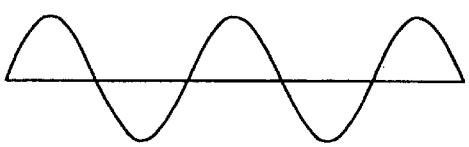
Figure 10F:
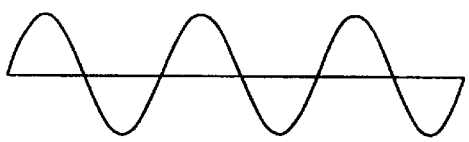
Figure 10G:
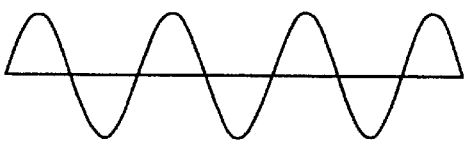
Figure 10H:
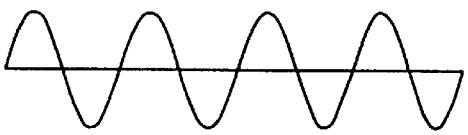
Figure 10I:
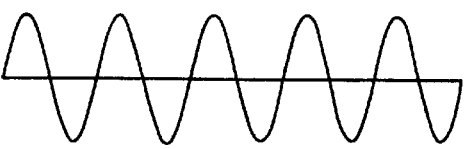
Figure 10J:
Figure 11A:
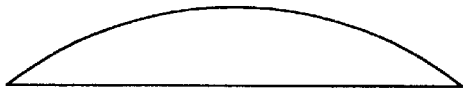
Figure 11B:
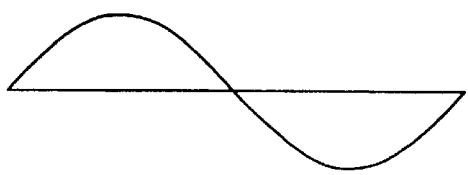
Figure 11C:
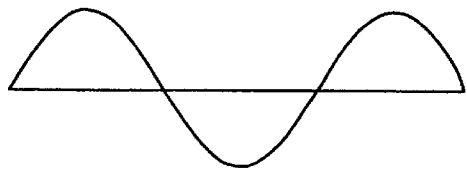
Figure 11D:
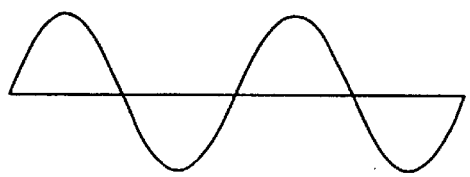
Figure 11E:
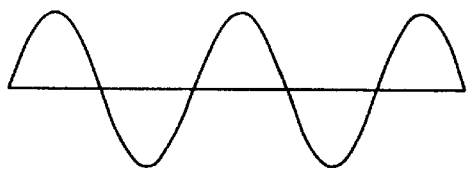
Figure 11F:
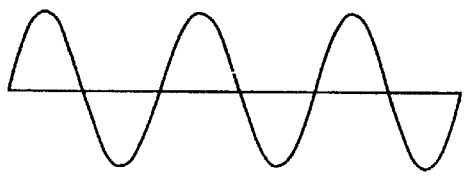
Figure 11G:
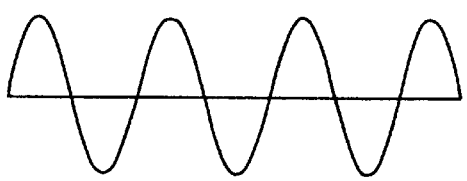
Figure 11H:
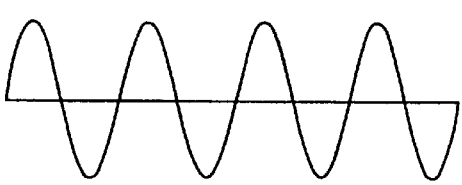

FIGS. 9D, 9E and 9F illustrates a multiphasic waveform showing the time domain representation in the left column and showing the frequency domain representation for patient impedance values of 39, 85 and 138 Ohms, respectively. This demonstrates a second impedance compensation method wherein individual and total pulse durations are kept constant (and unequal) and the frequency of stimulation is varied in a constant manner across the range of impedance variation.

FIGS. 10A to 10J shows ten 20 msec duration sinusoidal waveforms studied in a canine model of defibrillation, with transvenous electrodes. Frequency was varied from 25 to 300 Hz, which represents one-half through six complete cycles. Optimal waveforms corresponded to 75 to 112 Hz, with frequencies lower and higher than that range being inferior for defibrillation.

FIGS. 11A to 11H shows eight 40 msec sinusoidal waveforms studied in a canine model of defibrillation with transthoracic electrodes. Frequency was varied from 12.5 to 100 Hz, which represents one-half through four complete cycles. Optimal waveforms corresponded to about 87.5 Hz, with lower frequencies being inferior for defibrillation.

Figure 12A:
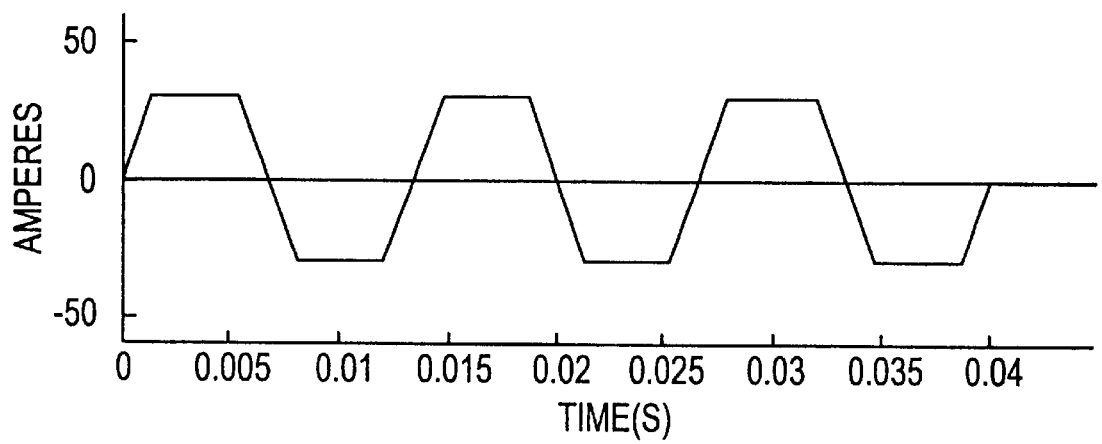

FIG. 12A shows a sinusoidal waveform with a duration of 40 milliseconds wherein the peaks of the waveform have been clipped at 60% of the peak current value.

Figure 12B:
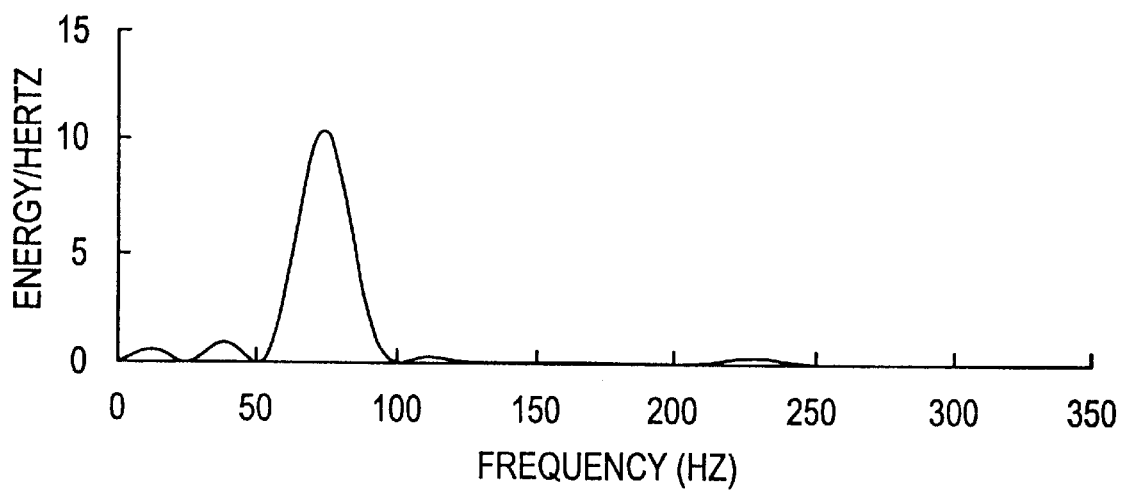

FIG. 12B shows the energy/Hertz representation of the Fourier transform of the waveform of FIG. 12A.

FIGS. 13A to 13I shows three families of waveforms that were studied in a canine model of external ventricular defibrillation, at each of three impedance levels (39, 85, and 138 Ohms), chosen to simulate average human impedance and two extremes.

FIG. 13J is a graph illustrating percent successful defibrillation along the y-axis (vertical axis) and simulated chest impedance along the x-axis (horizontal axis) for the Edmark, BTE and quadriphasic truncated exponential (QTE) waveforms at three simulated impedance levels (39, 85 and 138 Ohms) and at two delivered energies (18 and 24 Joules).

Figure 14:
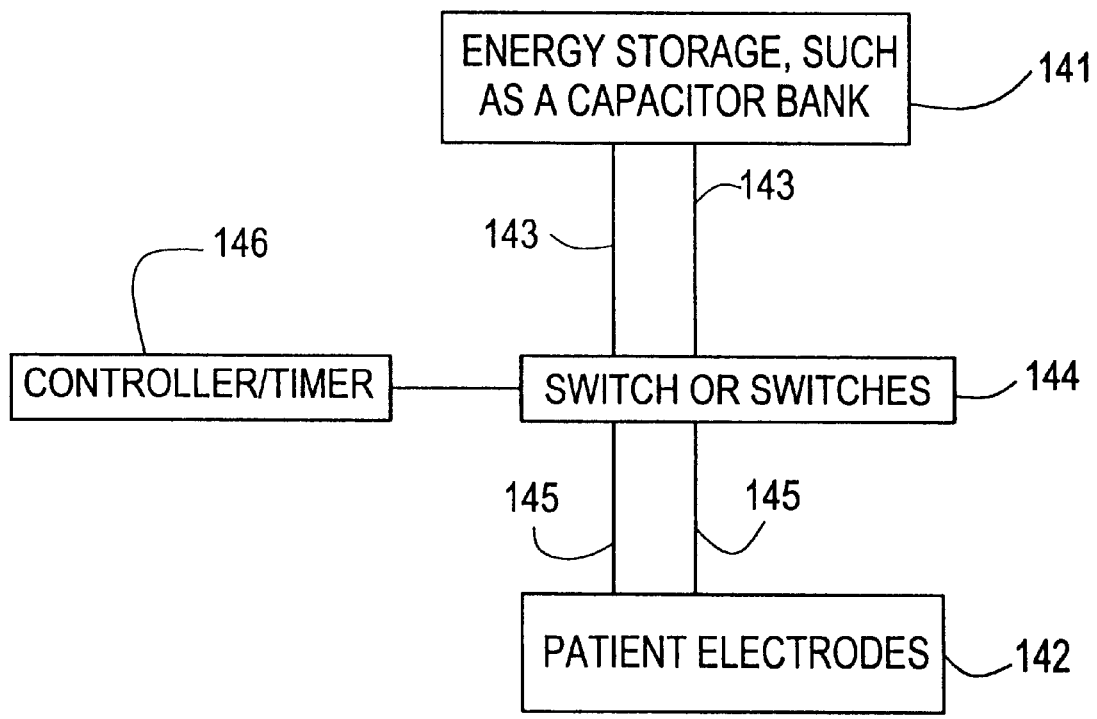

FIG. 14 is a block diagram of a clinical device according to the invention.

FIGS. 15A to 15H shows two families of truncated exponential waveforms, biphasic and multiphasic, and 4 durations, 6, 12, 18, and 24 msec. These two families of waveforms were studied in bothia canine model of internal ventricular defibrillation, and an ovine model of internal atrial defibrillation.

Figure 15A:
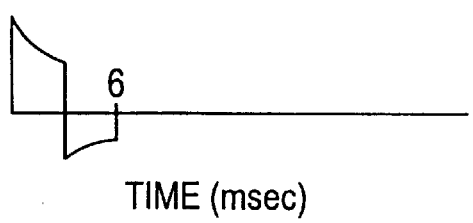
Figure 15B:
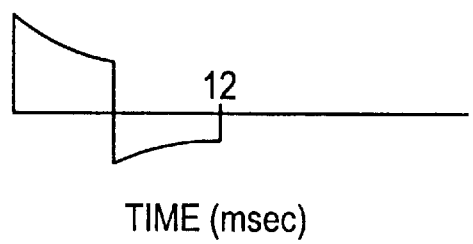
Figure 15C:
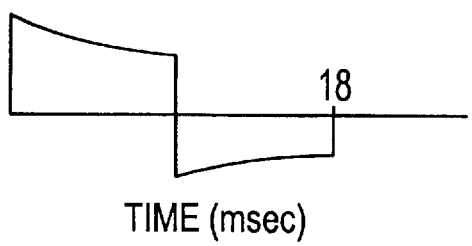
Figure 15D:
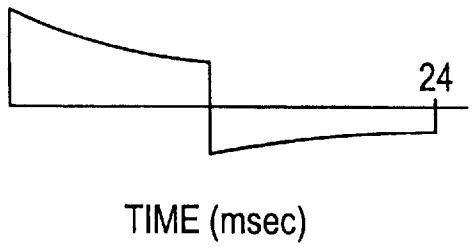
Figure 15E:
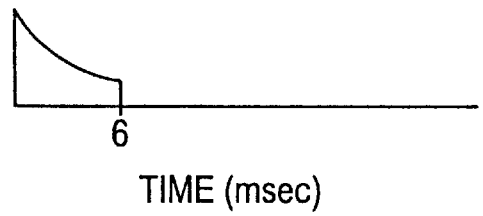
Figure 15F:
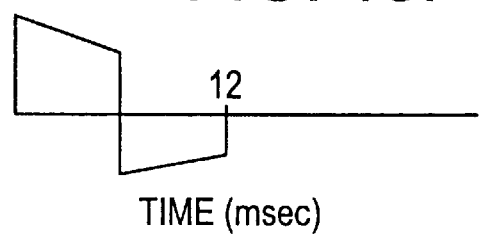
Figure 15G:
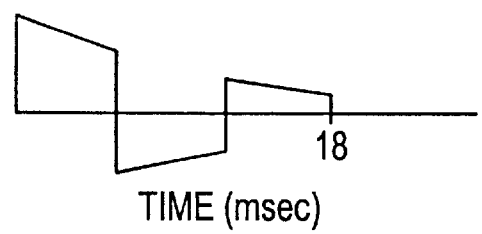
Figure 15H:
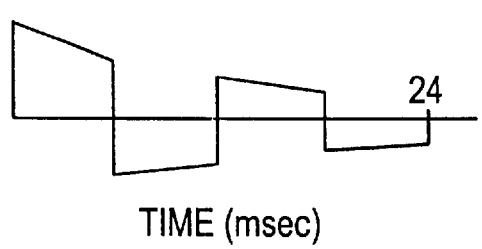
Figure 15I:
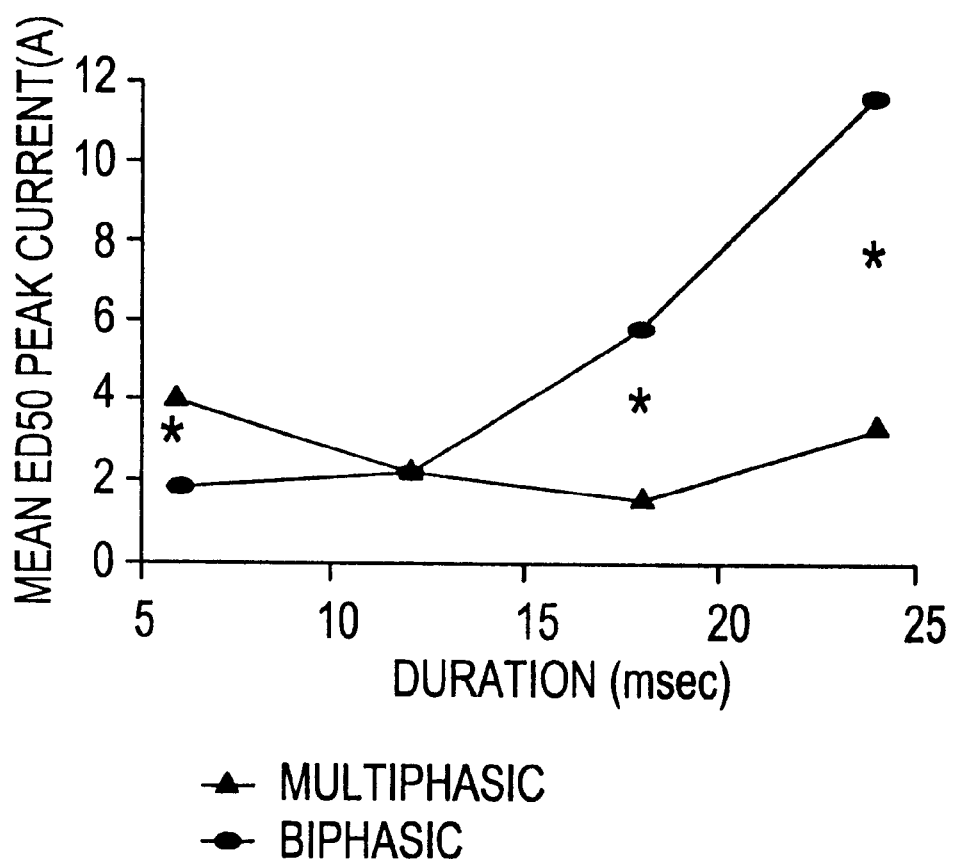

FIG. 15I is a graph illustrating the mean ED50 peak current for the biphasic and multiphasic waveforms of FIG. 15A, for treating atrial defibrlllation in an ovine model. The BTE waveform loses its efficacy at longer durations, whereas the multiphasic waveform retains its efficacy at longer durations, and with lower peak currents.

Figure 16:
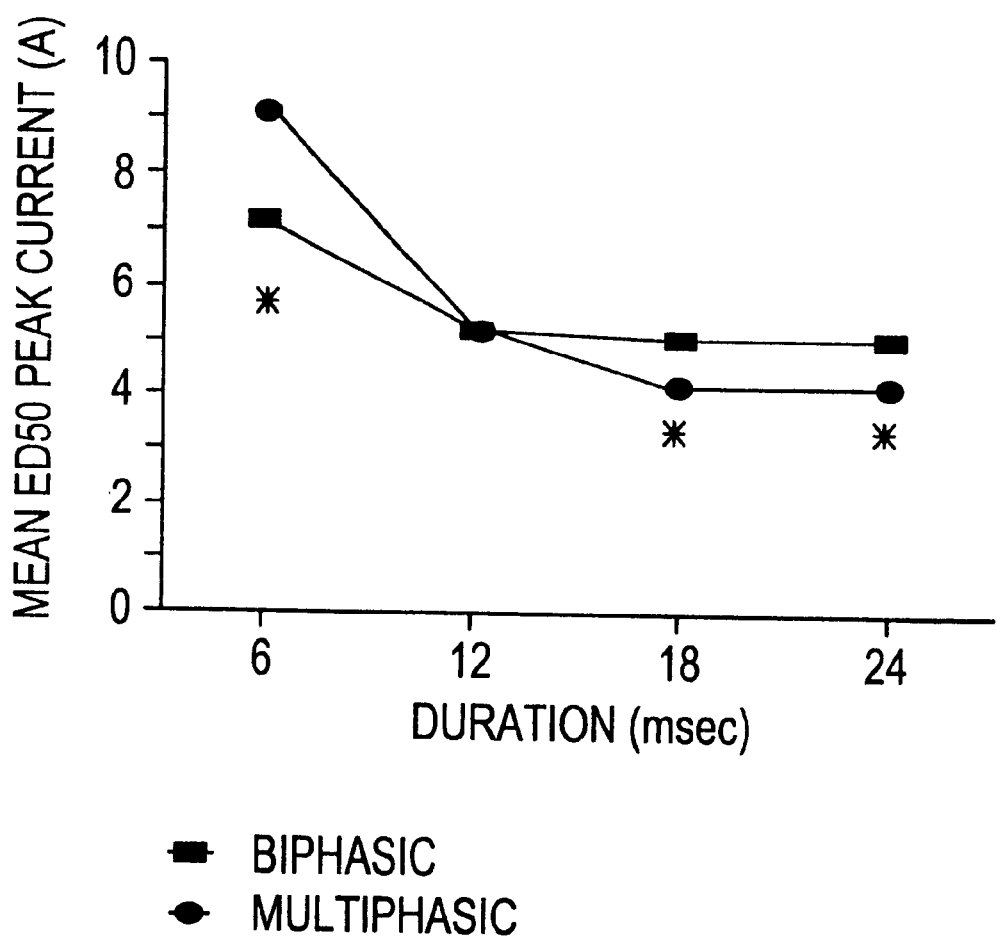

FIG. 16 is a graph illustrating the mean ED50 peak current for the biphasic and mulitiphasic waveforms of FIG. 15A, for treating ventricular defibrillation in a canine model. Here the BTE waveform retains its efficacy at longer durations, but the multiphasic waveform requires less peak current than the BTE the longer durations.

Figure 17A:
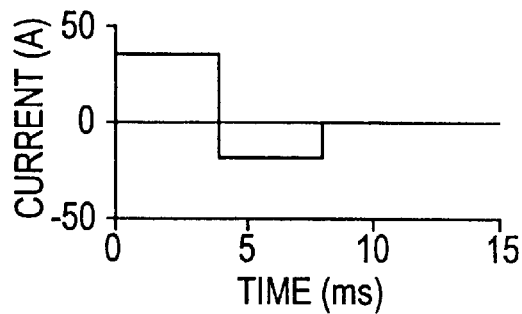
Figure 17B:
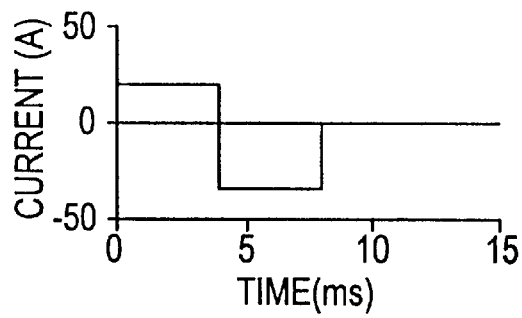

FIGS. 17A and 17B illustrate two biphasic waveforms: the waveform of FIG. 17A has a 35 A $1^{st}$ phase amplitude and an 18 A $2^{nd}$ phase amplitude; the waveform of FIG. 17B has an 18 A $1^{st}$ phase amplitude and a 35 A $2^{nd}$ phase amplitude.

Figure 17C:
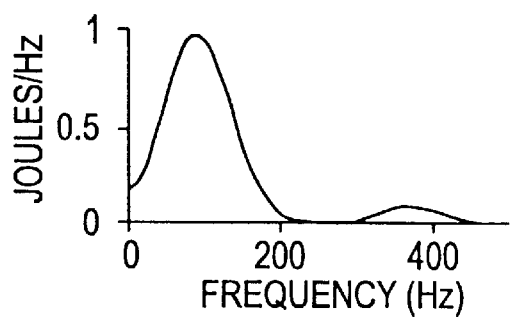
Figure 17D:
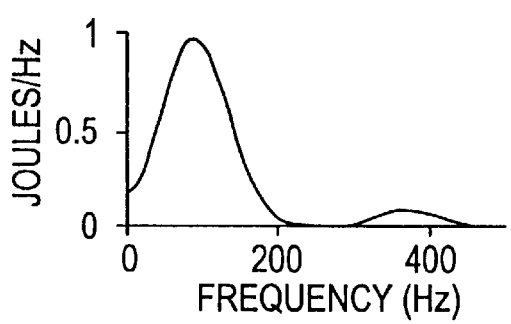

FIGS. 17C and 17D show the amplitude of the Fourier transform for each waveform of FIGS. 17A and 17B, respectively.

Figure 17E:
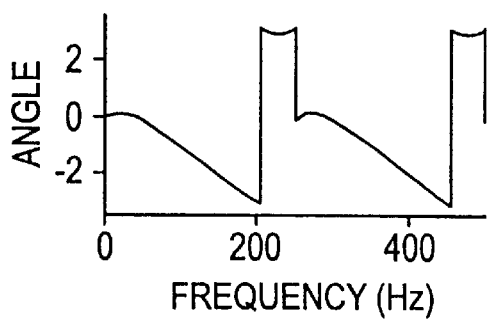
Figure 17F:
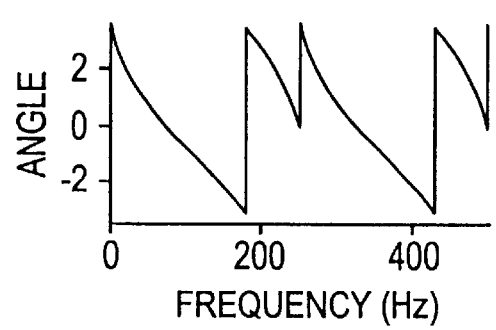

FIGS. 17E and 17F show the phase angle of the Fourier transform of each waveform of FIGS. 17A and 17B, respectively.

FIGS. 18A to 18E illustrates various waveforms that have the same duration and time constant of decay and are shown in the time domain.

FIGS. 18F to 18J illustrates various waveforms that have the same duration and time constant of decay and are shown in the frequency domain.

Table 1 shows the measured electrical parameters for the Edmark, BTE and QTE waveforms from the canine study of FIG. 15, at three simulated impedance levels (39, 85 and 138 Ohms) and at two delivered energies (18 and 24 Joules).

Corresponding reference characters indicate corresponding parts throughout the drawings.

DETAILED DESCRIPTION OF PREFERRED EMBODIMENTS

Figure 1A:
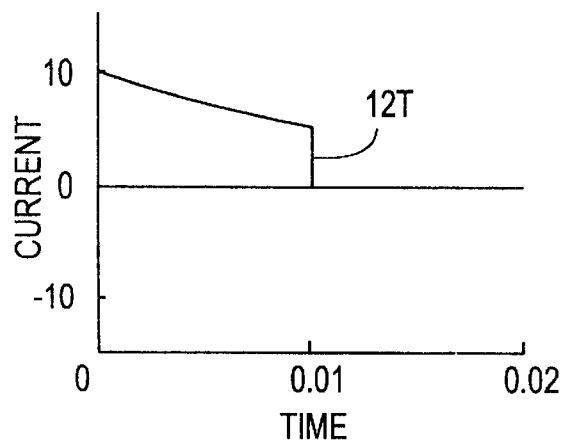
FIG. 1A illustrates a monophasic truncated exponential waveform showing the time domain representation.
Figure 1B:
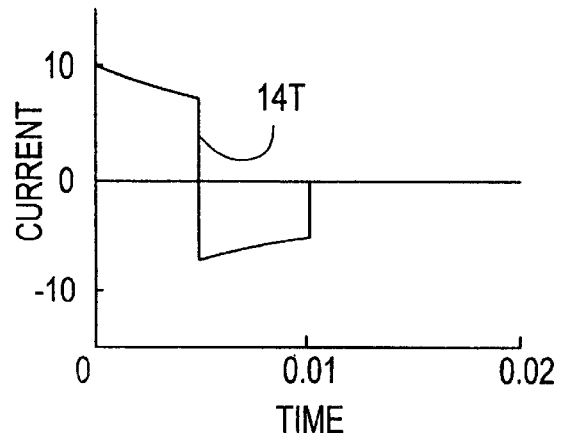
FIG. 1B illustrates a biphasic truncated exponential waveform showing the time domain representation.
Figure 1C:
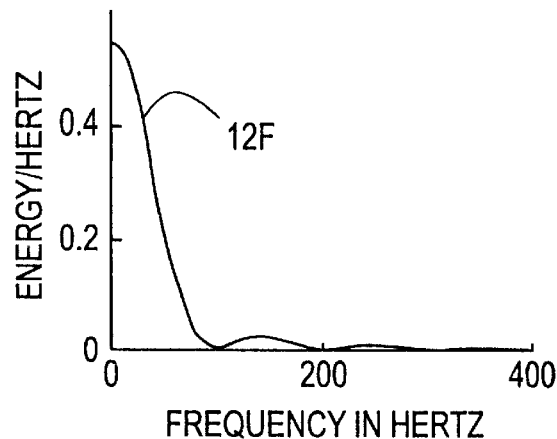
FIG. 1C illustrates a monophasic truncated exponential waveform showing the frequency representation.
Figure 1D:
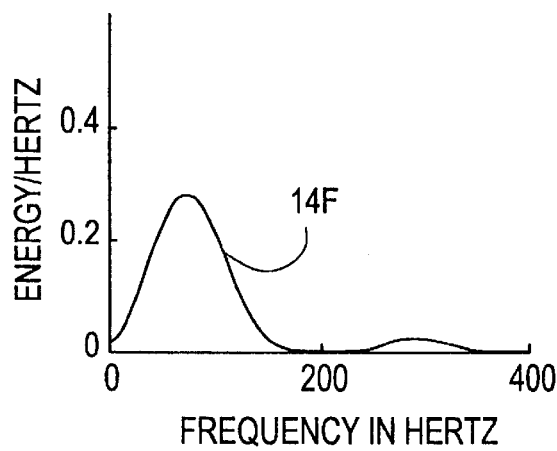
FIG. 1D illustrates a biphasic truncated exponential waveform showing the frequency domain representation.

A good analogy of frequency analysis is seen with the common prism, which separates white light into its component colors, or frequencies of light. In a similar manner, the Fourier transform identifies the frequency components which are present in any arbitrary electrical waveform. Although Fourier analysis is fundamental to many electrical engineering applications, it has not until recently been used to analyze the electrical waveforms used for electrical defibrillation. An example of frequency analysis can be found in FIGS. 1A to 1J, and 5A to 5F. In FIGS. 1A and 1B, two waveforms for defibryillation, a monophasic truncated exponential waveform (MTE) 12 and biphasic truncated exponential waveform (BTE) 14, are shown in the time domain referenced as 12T and 14F, respectively. In FIGS. 1C and 1D, two waveforms for defibrillation, a monophasic truncated exponential waveform (MTE) 12 and biphasic truncated exponential waveform (BTE) 14, are shown in the frequency domain referenced as 12F and 14F, respectively. The frequency domain representations in FIGS. 1C and 1D are plots of delivered energy as a function of frequency. Negative frequencies and phase angles are not shown here, and in most of the following analyses. As illustrated in FIGS. 1A and 1B, the effect of switching the polarity in the time domain to create a biphasic waveform has the effect of moving the dominant frequency lobe from 0 Hz to about 100 Hz in the frequency domain. The frequency content theory holds that the reason biphasic waveforms are superior to monophasic waveforms is that the energy is delivered in frequencies to which the heart is more responsive. There is some experimental evidence from defibrillation studies and from other studies of electrical stimulation of excitable tissues to suggest that this theory is better able to explain the phenomenon of defibrillation than are the RC circuit models. A frequency range of approximately 40 to 160 Hz has been identified, wherein the delivery of energy is associated with an increased efficacy for defibrillation.

Figure 1E:
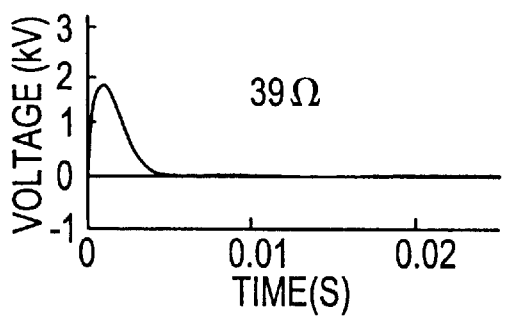
FIGS. 1E to 1G are prior art illustrations of a monophasic waveform of a typical Edmark defibrillator showing a time domain representation for impedance value of 39, 85 and 138 ohms, respectively.
Figure 1H:
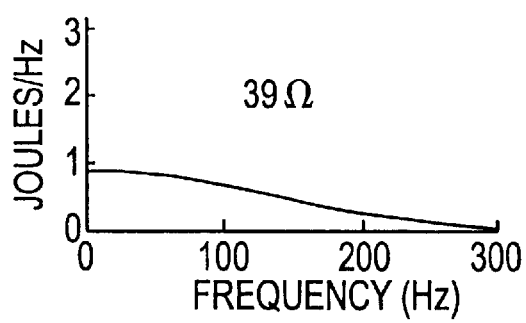
FIGS. 1H to 1J are prior art illustrations of a Fourier transform of a monophasic waveform of a typical Edmark defibrillator for impedance value of 39, 85, 138 ohms, respectively.
Figure 1F:
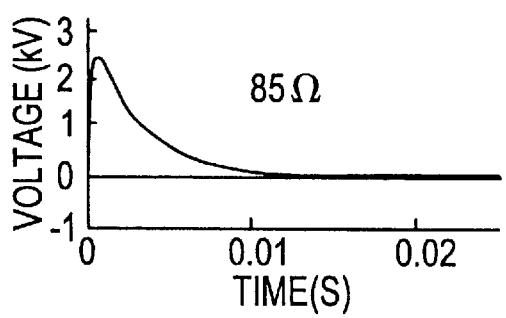
Figure 1I:
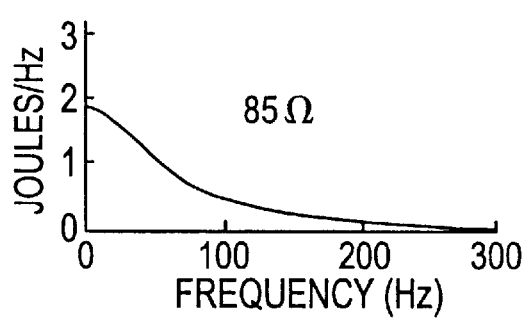
Figure 1G:
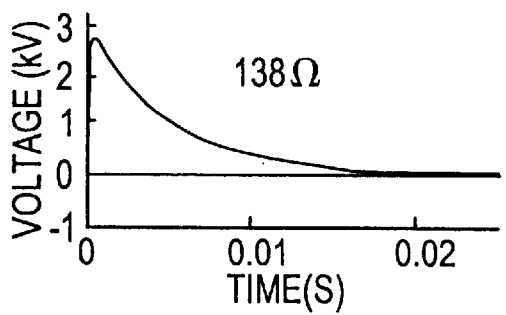
Figure 1J:
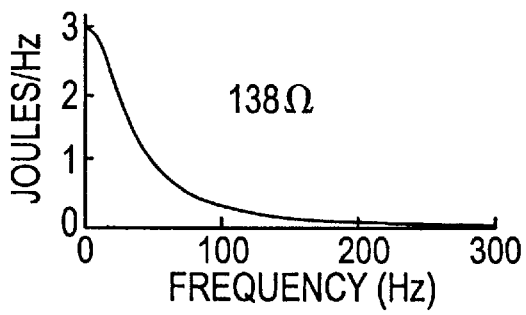
Figure 1K:
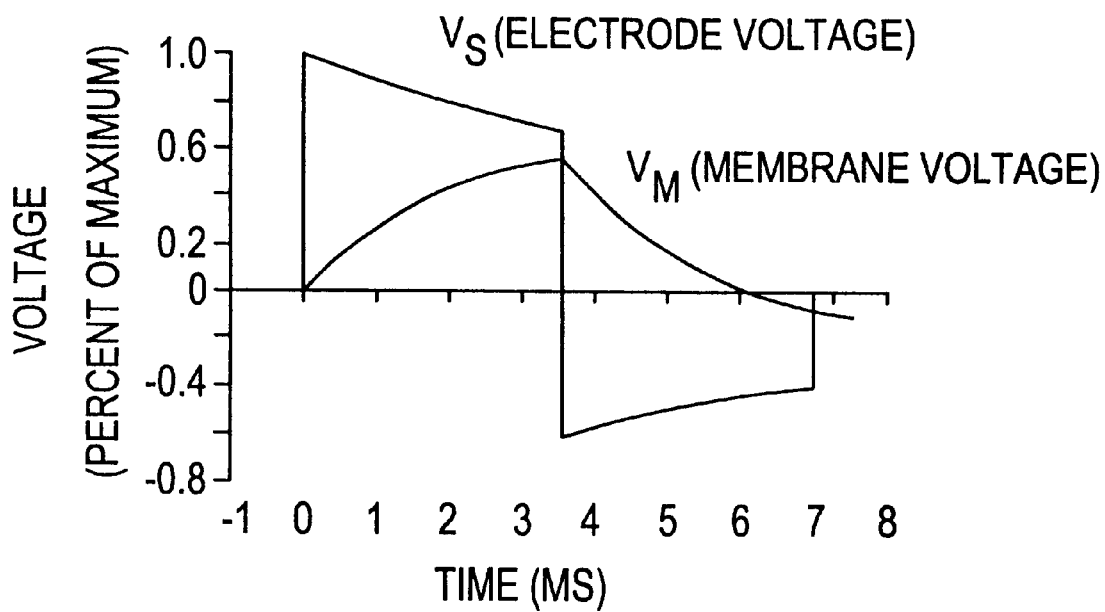
FIG. 1K is a graph illustrating the RC circuit model of defibrillation which postulates that a voltage $V_M$ builds on a membrane capacitance during the discharge of a defibrillation shock $V_S$. The biphasic waveform removes this charge and thereby improves efficacy.

Similarly, FIGS. 1E to 1G illustrate a monophasic waveform of a typical Edmark defibrillator showing the time domain representation for patient impedance values of 39, 85 and 138 ohms, respectively. FIGS. 1H to 1J illustrate a monophasic waveform of a typical Edmark defibrillator showing the frequency domain representation for patient impedance values of 39, 85 and 138 ohms, respectively. FIGS. 5A to 5C illustrate the output of a biphasic truncated exponential (BTE) waveform defibrillator, specifically the Heartstream FORERUNNER® defibrillator, showing a time domain representation for patient impedance values of 39, 85 and 138 ohms, respectively. FIGS. 5D to 5F illustrate the output of a biphasic truncated exponential (BTE) waveform defibrillator, specifically the Heartstream FORERUNNER® defibrillator, showing a frequency domain representation for patient impedance values of 39, 85 and 138 ohms, respectively. FIG. 1K is a graph illustrating the RC circuit model of defibrillation which postulates that a voltage $V_M$ builds on a membrane capacitance during the discharge of a defibrillation shock $V_S$. The biphasic waveform removes this charge and thereby improves efficacy.

Using the frequency content theory to optimize defibrillation waveforms according to this invention leads to very different waveforms than does optimization with the RC circuit models. The RC circuit models always yield biphasic waveforms, since one is charging the model to a maximal value and then discharging the model such that the final model response is very near zero. This is a two-step process, and therefore one only needs two phases. However, with the frequency content theory, the waveform is optimized such that it will deliver the maximum energy in approximately the 40 to 160 Hz range for ventricular defibrillation or ventricular cardioversion, with the dominant frequency lobe preferably centered near 100 Hz. The actual frequency range may vary from patient to patient and may vary based on such factors as impedance and types of electrodes, so that the center frequency may vary and may have to be determined experimentally. Optimizing the waveform for atrial defibrillation or cardioversion, yields a waveform that will deliver the maximum energy in approximately the 40 to 160 Hz range, with the dominant frequency lobe preferably centered near 125 Hz. Optimizing the waveform to reduce the stimulation of pain receptors during the shock for atrial defibrillation or atrial cardioversion, yields a waveform that will deliver the maximum energy in higher frequencies, which will need to be determined experimentally, but which may be approximately in the 1,000 to 2,000 Hz range. The actual frequency range may vary from patient to patient and may vary based on such factors as impedance and types of electrodes, so that the center frequency may vary so that it may have to be determined experimentally.

This process suggests a quite different waveform than the conventional biphasic waveform. Rather it suggests a multiphasic waveform (i.e., three or more pulses), in which the polarity is switched back and forth at approximately the desired peak of the dominant frequency lobe of the frequency domain representation. In one preferred embodiment, optimizing the amount of energy delivered in the desired frequency band is then the over-riding design parameter, which is then coupled with other design parameters specific to the particular application, to yield different optimal waveforms for different applications.

Human Transthoracic Defibrillation

In human transthoracic defibrillation, the impedance has been shown to vary over a much wider range, roughly 40 to 140 Ohms or greater, than is seen with internal defibrillation, roughly 35 to 65 Ohms. This presents a particular problem for human transthoracic defibrillators, especially those designed for the out-of-hospital, public access defibrillation market, where minimizing the size and weight of the defibrillators is critical. Many of these defibrillators on the market, have generated monophasic or biphasic truncated exponential waveforms. Truncated exponential waveforms have an advantage in this application over traditional waveforms, such as the Lown and Edmark waveforms, due to their not requiring the inclusion of an inductor in the waveform generation circuit. Inclusion of an inductor adds weight, size, and cost to the defibrillator; and requires the defibrillator to generate higher voltages than devices which use truncated exponential waveforms.

Figure 2A:
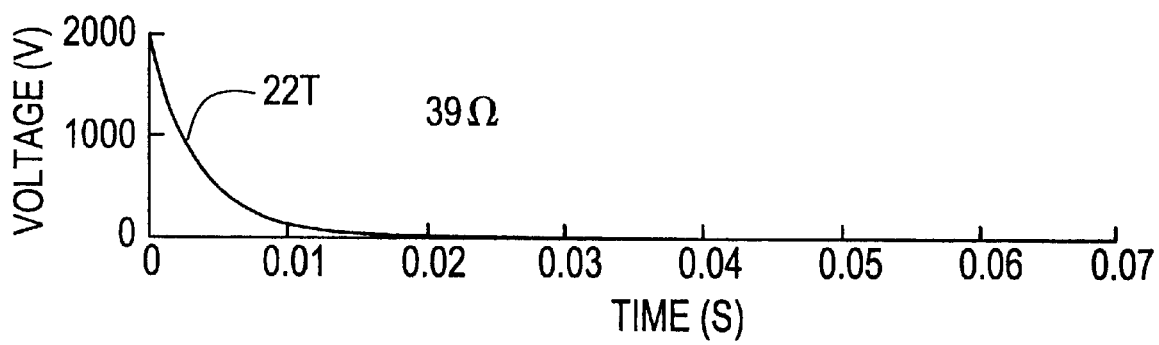
FIGS. 2A to 2C illustrate a monophasic untruncated exponential waveform for chest impedance values of 39, 85 and 138 ohms, respectively, and a 100 microfarad capacitor.
Figure 2B:
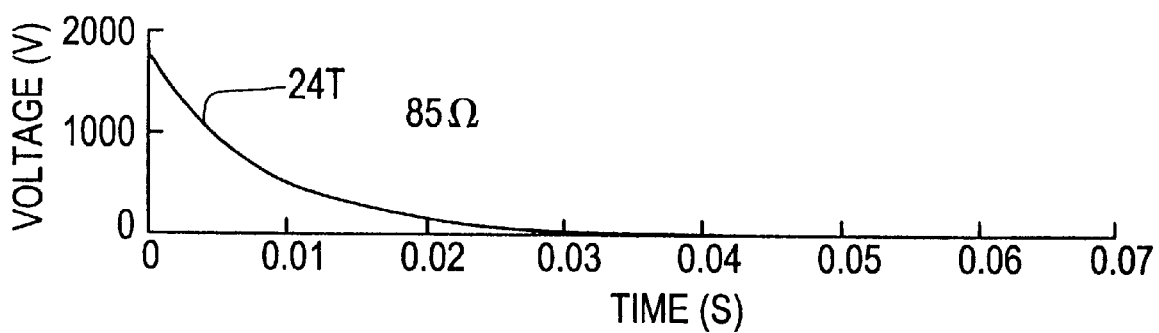
Figure 2C:
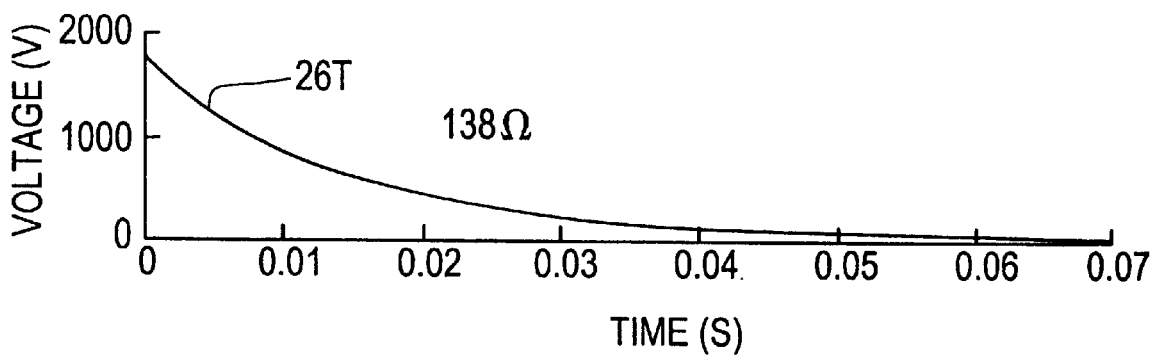

Typical truncated exponential waveforms are generated by charging a capacitor to a desired voltage, and then the discharge is initiated through the patient. The rate of decay of the capacitor voltage, called the time constant of decay of the resistor-capacitor (RC) circuit, will then be determined by the patient impedance, or resistance. A low patient impedance yields a short time constant, and a rapid decay of the voltage with time; whereas a high patient impedance yields a long time constant, and a slower decay of voltage with time. Typical monophasic untruncated exponential waveforms 22, 24 and 26, with varying chest impedances of 39, 85 and 138 Ohms, respectively, employing a typically sized capacitor (100 microfarads) are shown in FIGS. 2A to 2C. These figures illustrate the dramatically different voltage waveforms, if all are allowed to decay for greater than or equal to 5 time constants.

Biphasic waveforms, as a class, were shown to be more effective than monophasic waveforms in both transthoracic and internal defibrillation of animals by the MU lab in pioneering studies performed in the early 1980's. These waveforms have since been shown to be more effective in a variety of experimental animal models and in humans. In the last decade, biphasic waveforms have become the industry standard for implantable cardioverter-defibrillators (ICD) for human use. In doing so, the size and weight of ICDs have been reduced; and the effectiveness of the devices has improved.

However, it was only recently that biphasic waveforms have been utilized in human transthoracic defibrillation. Human studies have now been conducted with two different biphasic waveforms, the Gurvich waveform (a biphasic RLC waveform), and the several versions of the biphasic truncated exponential (BTE) waveform. Both waveforms have been reported to be superior to monophasic waveforms in defibrillation of humans in controlled clinical trials. The BTE waveforms have now been incorporated into several clinical devices that have been approved for use in humans. Early reports of the use of these devices in out-of-hospital cardiac arrest have been consistent with the studies out of the MU lab, and have likewise concluded that the BTE waveform is generally more effective than standard monophasic waveforms in transthoracic defibrillation.

Impedance Compensation Strategies

Figure 3A:
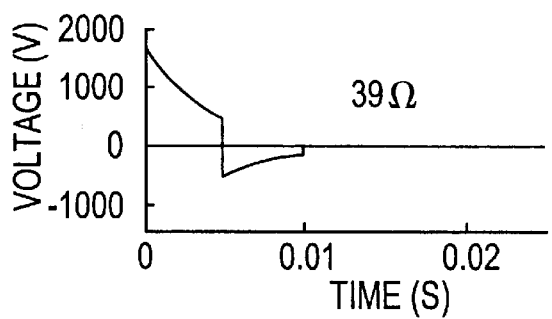
FIGS. 3A to 3C illustrate a manual impedance compensation method showing a biphasic truncated exponential waveform having constant phase and overall pulse durations with the time domain representation for patient impedance values of 39, 85 and 138 ohms, respectively.
Figure 3D:
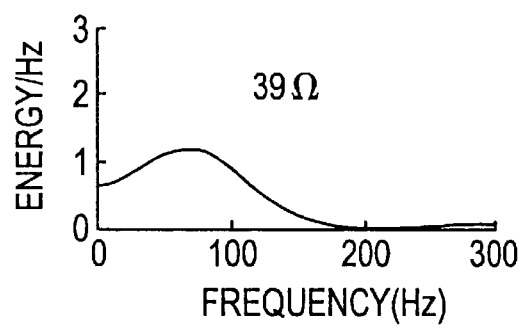
FIGS. 3D to 3F illustrate a manual impedance compensation method showing a biphasic truncated exponential waveform having constant phase and overall pulse durations with the frequency domain representation for patient impedance values of 39, 85 and 138 ohms, respectively.
Figure 3B:
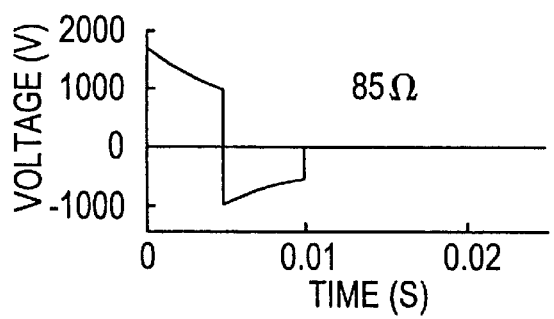
Figure 3E:
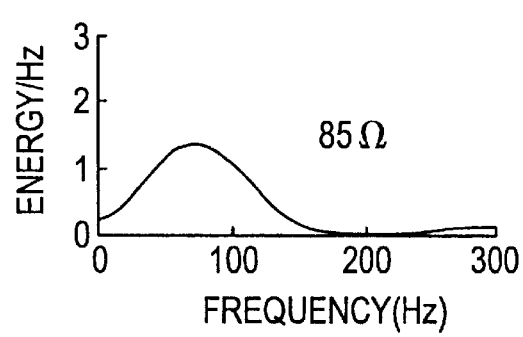
Figure 3C:
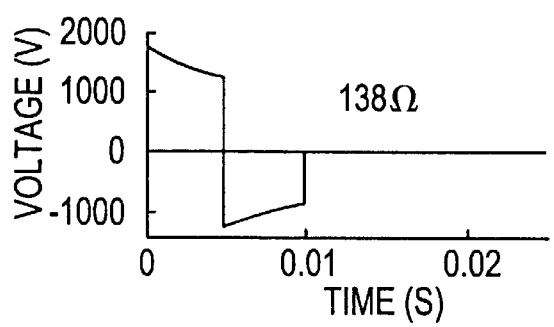
Figure 3F:
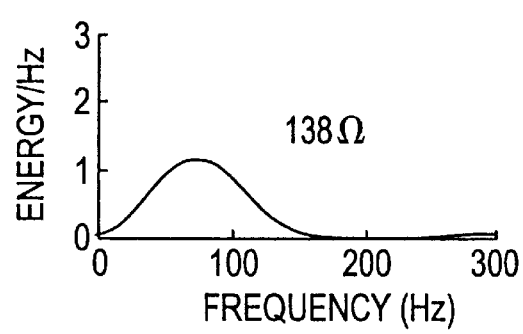

As shown in FIGS. 2A to 2C, an RC defibrillator will exhibit different rates of decay when applied to patients that exhibit different impedances. The manner in which the generated waveform changes when applied to different impedances will herein be called the impedance compensation strategy. The strategies can be broadly grouped into passive strategies, where waveform changes can be described by basic circuit theory; and active strategies, where an active intervention is superimposed on the basic waveform changes. One passive strategy, which has been called the manual method in the ICD industry, is to program a fixed time duration for each pulse, and let parameters such as final voltage and the voltage at which the polarity is switched vary depending on the patient impedance. Representative BTE waveforms that would be generated with the manual method, with a fixed overall duration of 10 milliseconds are shown in FIGS. 3A to 3F. FIGS. 3A to 3C show three BTE waveforms having constant individual phase and overall pulse durations, with the time domain representation for patient impedance values of 39, 85 and 138 ohms, respectively. FIGS. 3D to 3F show three BTE waveforms having constant individual phase and overall pulse durations, with the time domain representation for patient impedance values of 39, 85 and 138 ohms, respectively. A disadvantage of this method, is that the amount of energy that is delivered by these waveforms to patients in response to different impedances, will vary widely.

Figure 4A:
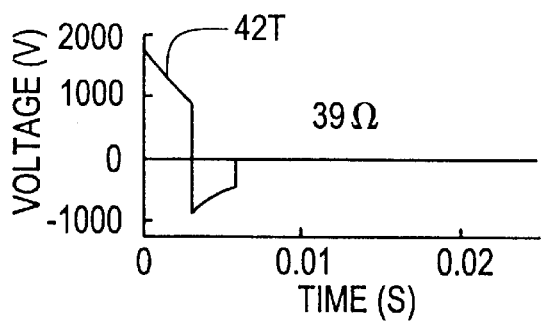
FIGS. 4A to 4C illustrate a voltage-based (also called automatic) impedance compensation method, showing a biphasic truncated exponential waveform, wherein the initial and final voltages of each phase are constant with variations in impedance, with the time domain representation for patient impedance values of 39, 85 and 138 ohms, respectively.
Figure 4D:
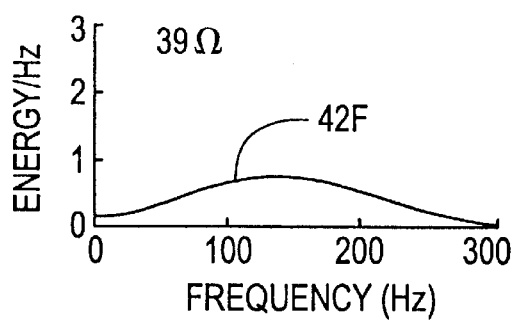
FIGS. 4D to 4F illustrate a voltage-based (also called automatic) impedance compensation method, showing a biphasic truncated exponential waveform, wherein the initial and final voltages of each phase are constant with variations in impedance, with the frequency domain representation for patient impedance values of 39, 85 and 138 ohms, respectively.
Figure 4B:
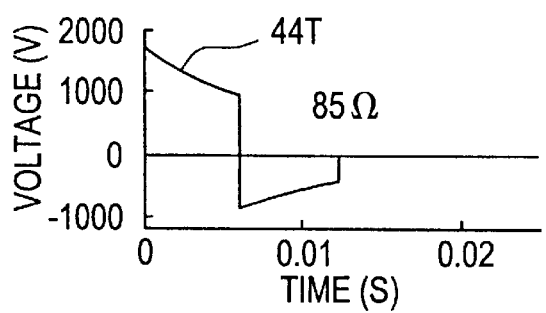
Figure 4E:
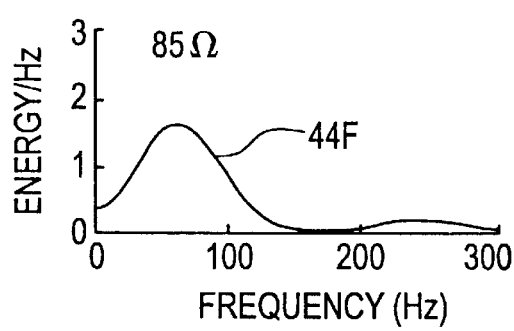
Figure 4C:
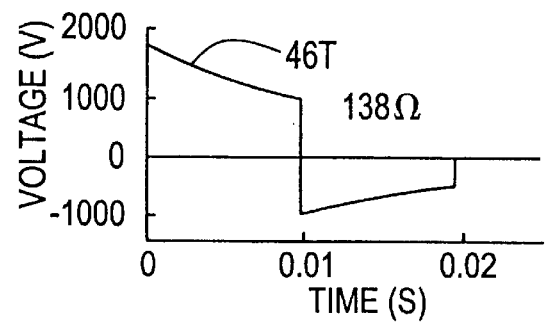
Figure 4F:
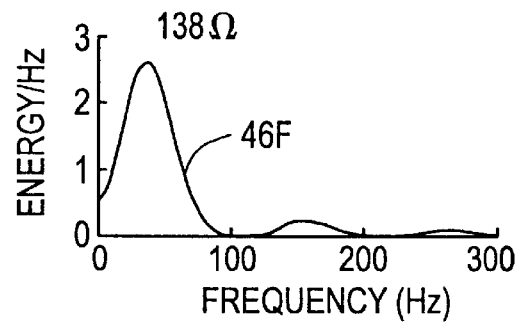

Although delivered energy has been shown to not be a good parameter for predicting defibrillation success, devices that keep the delivered energy constant across patient impedances are desirable for some applications. An impedance compensation strategy which has been used in many ICDs and monophasic truncated exponential waveform transthoracic defibrillators is a voltage based method, which is also called the automatic method. This active impedance compensation strategy fixes the initial and final voltages of each pulse, and therefore these can also be called fixed tilt waveforms. The tilt is usually defined as the percentage change in either voltage or current of a truncated exponential pulse. One variation of the automatic method of generating BTE waveforms is shown in FIGS. 4A to 4F. Here the polarity of the discharge is switched when the voltage has decayed to a value that will yield equal phase durations, and the second phase is terminated when the final voltage has decayed to 25 percent of the first phase initial value. This strategy will give a constant delivered energy, and constant initial and final voltages on each pulse delivered. However, one disadvantage is that the individual and total pulse durations will vary directly with patient impedance. FIG. 4A shows that a 39 Ohm patient with this strategy will receive a waveform 42T with an overall duration of 5.4 msec. However, an 85 Ohm patient will receive a waveform 44T with an overall duration of about 12 msec, as shown in FIG. 4B, and a 138 Ohm patient will receive a waveform 46T with an overall duration of about 19 msec, as shown in FIG. 4C. Waveform impedances more extreme than these values will yield correspondingly more extreme values of total pulse duration. Also shown in FIGS. 4D to 4F are the energy/Hz representation 42F, 44F and 46F of the Fourier transform of each waveform 42T, 44T and 46T, respectively. As the overall duration is shortened, the dominant frequency lobe of the transform is moved to higher frequencies; and as the overall duration is lengthened, the dominant frequency lobe of the transform is moved to lower frequencies. Both of these changes have the effect of delivering less energy in the optimal frequency range (40 to 160 Hz).

A major disadvantage to the automatic method of impedance compensation, when applied to transthoracic defibrillation, is that both monophasic and biphasic waveforms have been shown to lose their efficacy at very long and very short pulse durations. Therefore, when patients exhibit the extremes of humans impedance values, the efficacy of a MTE or BTE waveform will be decreased. A variation of the automatic method has been chosen by Heartstream, the makers of the FORERUNNER® device, to put limits on the pulse duration variation utilized in their version of the automatic method of impedance compensation, which can be classified as an active strategy. Based on published reports, their method limits the pulse duration to a range of 8 msec to 20 msec. In addition, this device modifies the durations of the individual phases of the BTE waveform, and the ratio of the durations of the two phases in response to the patient impedance measured during the discharge. FIGS. 5A to 5C show waveforms 52T, 54T and 56T generated with this variation of the automatic method of impedance compensation, at 39, 85 and 138 Ohms, respectively. FIGS. 5D to 5F show waveforms 52F, 54F and 56F of the energy/Hz representations for each of the biphasic waveforms 52T, 54T and 56T, respectively. By limiting the shortest duration to 8 msec, rather than the 5.4 msec of the automatic method, waveform 52F of FIG. 5D shows that this method delivers more of the energy in the optimal frequency band with the low impedance patients. However, by lengthening the first pulse duration relative to the second in high impedance patients, this method shifts the dominant frequency lobe to even lower frequencies than does the automatic method, and delivers even less energy in the desired frequency band as shown by waveform 56F of FIG. 5F.

FIGS. 6A to 6C show representative waveforms for the automatic method of impedance compensation for 39 Ohms, 85 Ohms and 138 Ohms, respectively. FIGS. 6D to 6F show representative waveforms for the manual method of impedance compensation for 39 Ohms, 85 Ohms and 138 Ohms, respectively. FIGS. 6G to 6I show representative waveforms for the Heartstream's FORERUNNER® method of impedance compensation for 39 Ohms, 85 Ohms and 138 Ohms, respectively. This figure also indicates the energy in joules (J) which would be delivered at each of the assumed impedance values. One can see that the automatic method of FIGS. 6A to 6C does the best job of delivering a constant energy of about 143 J, while the manual method of FIGS. 6D to 6F delivers a constant pulse duration while varying the energy from 153 J to 126 J and the Heartstream Forerunner method of FIGS. 6G to 6I delivers pulses of energy varying from 150 J to 144 J.

Therefore, one aspect of this invention is that it is better to keep the frequency of stimulation constant rather than the waveform appearance in the time domain. I believe this to be particularly advantageous whenever longer duration waveforms are required (such as to reduce peak current), and when longer duration waveforms are produced by high impedance patients. My theory is that a multiphasic waveform, optimized to keep the switching frequency at the optimal frequency, will be more effective than a biphasic waveform at equal durations especially equal durations at longer periods. A recent study examined the eight waveforms shown in FIGS. 7A to 7H in a canine model of defibrillation with transvenous electrodes. This figure shows four biphasic waveforms 71T, 72T, 73T and 74T of FIGS. 7A to 7D, with durations of 6, 12, 18, and 24 msec, respectively. FIGS. 7E to 7H show four multiphasic waveforms 75TF, 76T, 77T and 78T, where each phase duration is 6 msec, and the overall pulse duration is the same as the waveforms on the left. In this study, the multiphasic waveform yielded lower current ED50s at both 18 and 24 msec than did the biphasic sinusoidal waveforms. This data supports the advantages of the present invention over the industry standard biphasic waveforms.

A) Representative Applications of This Invention to Transthoracic Atrial or/or Ventricular Defibrillation In the following discussion, a representative waveform is given, assuming a capacitor size of 100 microfarads, a mean chest impedance of 85 ohms, an optimal switching frequency of 100 Hz, and a maximum duration of 20 milliseconds. All of these parameters would have to be optimized experimentally depending on the particular application, and therefore these are only representative waveforms, which are not meant to limit the scope of the present invention. Likewise, generating these waveforms with an RC circuit is not meant to be the only way to maximize the energy delivered in a desired frequency band. The best way to maximize the energy delivered at a given frequency is by generating a long duration sinusoidal waveform. This is not a practical waveform for many applications, but multiphasic trapezoidal and modified sinusoidal waveforms can be designed using the teachings of this invention.

In one embodiment of the present invention, a truncated exponential waveform is generated as an RC circuit with a typical sized capacitor (100 microfarads), and the polarity of the discharge is switched back and forth to yield a multiphasic waveform with constant individual pulse durations, here taken to be 5 msec. By delivering only 5 msec duration pulses, the dominant frequency lobe will stay centered very near 100 Hz, which is near the center of what I believe to be the optimal frequency band, which will be determined experimentally. The multiphasic waveforms generated by this embodiment of the present invention are shown in FIGS. 8A to 8F, where the impedance values chosen are again those used above. Waveforms 82T, 84T and 86T of FIGS. 8A to 8C are time domain representations and waveforms 82F, 84F and 86F of FIGS. 8D to 8F are their corresponding frequency domain representations for impedances of 39, 85 and 138 Ohms, respectively.

In addition to the switching rule, one needs a rule for stopping the discharge. In this embodiment of the invention, the stopping rule is taken to be a total pulse duration of 20 msec. Therefore, with low impedance patients, the capacitor is allowed to discharge to very near zero volts. Our laboratory has previously demonstrated that one need not truncate a short time constant monophasic waveform, and this is expected to also be the case with short time constant multiphasic waveforms. With high impedance patients, the time constant of decay is the same as the other methods of impedance compensation, as it must since the time constant is determined by the capacitor size and the patient impedance. Here, by keeping the switching frequency constant, this method delivers a fixed number of pulses (4 in this example), after which the pulse is terminated (in this example) at a total duration of 20 msec. This is done as the MU laboratory has previously demonstrated that long time constant monophasic truncated exponential waveforms need to be truncated for optimal efficacy, and I expect this relation to also hold for multiphasic waveforms. Also shown in FIGS. 8A to 8F are the energy/Hz representation of the Fourier transform for these waveforms. One can see that this method keeps the dominant frequency lobe centered very close to the 100 Hz target. This 100 Hz target, and therefore the individual pulse durations, may be changed based on prospective experimental results in animal models, and may in fact be found to be different for animals and humans.

In a second embodiment of this invention, the capacitor is again assumed to be 100 microfarads, and the patient impedance is taken to vary from 39 to 138 Ohms. The individual pulse duration is again taken to be 5 msec, which fixes the dominant frequency lobe of the transform very near 100 Hz. In this embodiment of the invention, the capacitor voltage is monitored, and no new pulses are initiated if the voltage is measured to have fallen below a threshold value (here taken as 25% of the initial voltage) when measured during the inter-pulse time delay. Waveforms generated with this embodiment of the present invention are not shown, but would be similar to those in FIGS. 8A to 8F, with no pulses having initial voltages of less than 437.5 volts. In this embodiment, the lowest impedance patients may only be given two or three pulses, but the pulse durations will be maintained constant. The dominant frequency lobe is again kept constant in this method, but delivered energy values will be slightly different from those calculated in the first embodiment of this invention. This 100 Hz target, and therefore the individual pulse durations, may be changed based on prospective experimental results in animal models, and may in fact be found to be different for animals and humans.

In a third embodiment of the present invention, the individual pulse durations are again fixed at 5 msec, However the stopping rule is now chosen to terminate all pulses when the capacitor voltage has decayed to 25% of its initial voltage. Waveforms from this embodiment of the present invention are not shown, but would be similar to those in FIGS. 8A to 8F, only all pulses would be truncated when the electrode voltage decreased to 25% of the initial voltage of the first phase. This version has the distinction of shortening the final pulse duration, when the impedance reaches the programmed threshold. This version has the advantage of keeping the dominant frequency lobe centered at the desired frequency, and also keeping the total delivered energy constant. Total pulse duration varies over a smaller range of values than is seen with the automatic method. Once again, the dominant frequency lobe would be expected to stay very close to the 100 Hz target. This 100 Hz target, and therefore the individual pulse durations, may be changed based on prospective experimental results in animal models, and may in fact be found to be different for animals and humans.

In a fourth embodiment of this invention, the individual pulse durations are allowed to vary in a prescribed manner, but are not changed with different impedance patients. Experimental studies in the past have demonstrated that there is an advantage to having the first pulse duration be the same as, or larger than the second pulse duration. In the event that further experimental studies demonstrate an advantage to pulses with a prescribed variation in the individual pulse durations, this embodiment of the present invention would vary pulse durations for each of the pulses generated. FIGS. 9A to 9F show representative waveforms generated with this method with the same patient impedances used above. Waveforms 92T, 94T and 96T of FIGS. 9A to 9C are time domain representations and waveforms 92F, 94F and 96F of FIGS. 9D to 9F are frequency domain representations for impedances of 39, 85 and 138 Ohms, respectively. In this example, the individual pulse durations are fixed in the following order: 6 msec, 5.5 msec, 4.5 msec, and 4 msec, but they could take on any value, after experimental studies. The important feature differentiating this embodiment of the present invention, is that all pulses are given with fixed durations, in the prescribed order, and the stopping rule is here taken to be 20 msec total duration. The energy/Hz representation of each of these waveforms is also shown in FIGS. 9A to 9F.

In a fifth embodiment of the present invention, the individual pulse durations are fixed in a prescribed order as in the fourth embodiment of this invention. However, now the stopping rule is taken to be such that no new pulses are allowed to start, if the capacitor voltage is less than a fixed programmed value (here assumed to be 25% of the initial voltage). This prevents low amplitude pulses from being initiated, while maintaining the individual pulse durations constant with variations in patient impedance. Representative waveforms from this embodiment of this invention are not shown, but would be very similar to those shown in FIGS. 9A to 9F, without the small amplitude phases.

In a sixth embodiment of the present invention, the individual pulse durations are fixed in a prescribed order as in the fourth embodiment of the invention. However, now the stopping rule is taken to be that when the capacitor voltage drops below a programmed threshold (here 25% of the initial voltage), all pulses are immediately terminated. Representative waveforms from this embodiment of the present invention are again not shown, but would be similar to those of FIGS. 9A to 9F, for the same variation in patient impedance. This embodiment would have the feature of shortening the final pulse duration, when the threshold voltage has been reached.

B) Representative Applications of This Invention to Internal Atrial Defibrillation Atrial defibrillation has been hampered by poor patient acceptance of the electric shock required to reverse atrial fibrillation. Early animal research on internal atrial defibrillation suggested optimal phase durations for a biphasic truncated exponential (BTE) waveform of 3 msec for each phase. However, human studies found that durations of 6 msec for each phase worked just as well, and was tolerated better by the patient. The following are examples of the application of this invention to reduce the pain of atrial defibrillation. Some of these waveforms may not be convenient to generate in implantable units. However, one application of these principles would involve internal atrial defibrillation shocks generated by an external pulse generator. Many more waveforms would be possible in this application, than are possible in implantable devices. The following examples are divided into two categories.

Defibrillate With a Longer Duration Multiphasic Waveform of Optimal Frequency

Zoll et al reduced the pain of external cardiac pacing by increasing the pulse duration to 40 ms, and using a constant current amplitude. Zoll reasoned that this reduced the peak current below the pain threshold for electrical stimulus of the skin. Assuming a similar mechanism for pain in atrial defibrillation, one could utilize a relatively constant current monophasic shock of longer duration (to reduce peak current) for defibrillation; but in animal studies, this has not proven to be a very effective waveform for defibrillation. Our previous work in transthoracic ventricular defibrillation of calves demonstrated that for constant current pulses of both 35 A and 50 A, the efficacy decreased as the pulse was lengthened from 16 to 32 ms. In a similar study of biphasic rectangular waveforms, our laboratory found again that with both 35 A and 50 A, the efficacy decreased as the pulse duration was lengthened from 16 to 32 ms.

More recently, at the 1996 NASPE meeting, there was an abstract presented that tried two different capacitance values and varied the pulse duration (up to 52 ms), in an effort to reduce the peak voltage required for atrial defibrillation. This study found that as the pulse duration of a biphasic pulse is increased, the voltage required to defibrillate stays the same, or increases, which means the delivered energy required increases at longer durations. Yet another study at NASPE found that larger capacitors and longer durations (up to 20 ms total) could reduce peak voltage from that seen with a 6 ms total duration. However, still longer durations that would reduce the required peak voltage or current further would seem to be desirable. Very long mono- or bi-phasic waveforms (e.g. 40 to 50 ms total) which could be generated by implantable devices, also have the common feature of a long tail, which has been implicated in causing refibrillation. Therefore, it appears that increasing the duration of the shock to lower the current (or voltage), will not yield a less painful and yet effective waveform, at least with the two waveforms most often used for internal defibrillation.

However, I recently conducted two studies while I was at the University of Alabama on a traveling fellowship sponsored by NASPE, where I studied the use of sinusoidal waveforms for ventricular defibrillation. These studies, while conducted for the purpose of trying to elucidate the mechanism of defibrillation, suggest that multiphasic sinusoidal waveforms will retain their efficacy as the duration is increased to 20 or 40 msec, and possibly longer. In a study with transvenous electrodes, the 10 waveforms of FIGS. 10A to 10J were studied in a canine model, where the frequency was varied from 25 to 300 Hz. I found that the ED50 (50% effective dose) for current at the optimal frequency (75 Hz) with a duration of 20 ms was 3.2 A, which yields a delivered energy of 7.1 joules, which is comparable to that observed with biphasic waveforms in this model. At 75 Hz, this sinusoidal waveform consists of 1½ full cycles. Further statistical analysis of theses data, put the optimal frequency at around 112 Hz, but further study would be necessary to pick the exact optimal frequency.

In the other study done at UAB with external electrodes, I studied the 8 waveforms of FIGS. 11A to 11H, also in a canine model. I found that the ED50 for current at the optimal frequency (about 87.5 Hz) was about 6.0 A, for a delivered energy of 47 joules, which is somewhat higher than, but comparable to that seen with biphasic waveforms in this model. At 87.5 Hz, this waveform consists of 3½ complete cycles. These two studies demonstrate that multiphasic sinusoidal waveforms can achieve ventricular defibrillation at delivered energies that are comparable to those seen with biphasic waveforms. Additional studies are needed to determine the limits of duration increase possible before unacceptable adverse effects on defibrillation efficacy are seen. However, the two studies already done indicate that multiphasic sinusoidal waveforms of up to 40 msec are effective waveforms for electrical defibrillation of the ventricles, and they require less peak current than presently used waveforms.

In surveying the literature on atrial defibrillation, it is observed that the waveforms that have been the most effective for ventricular defibrillation, are also proving to be the most effective for atrial defibrillation. Therefore it is reasonable to extrapolate data from ventricular defibrillation to predict efficacy with atrial defibrillation. Using such an assumption, I can hypothesize that atrial defibrillation with sinusoidal waveforms should be possible at delivered energies that are comparable to those observed with biphasic waveforms. Using a biphasic truncated exponential waveform for atrial defibrillation (with the standard RA-CS electrode configuration) requires about 2.5 joules, or about 220 Volts. Assuming 60 Ohms resistance, this is about 3.7 Amps (A) for the leading edge current. Delivering this same 2.5 joules with a 40 ms sinusoidal waveform would lower the peak current required to 1.02 A (rms), or 1.4 A (0-pk). Reducing the peak current from 3.7 A to 1.4 A, would likely lower the current below the pain threshold. Even if this waveform requires somewhat higher energy, the peak current will still be approximately one-half of that seen with the best biphasic waveforms.

Generating sinusoidal waveforms in devices which would be small enough to be implanted would be an engineering challenge. Sinusoidal waveforms could be generated by an external device that was connected to temporary internal electrodes for internal atrial defibrillation. In this application, the peak current may be reduced still further by clipping the peaks off of a sinusoidal waveform, or one could generate an alternating square wave with the desired frequency. FIG. 12A shows a 40 msec sinusoidal waveform, where each peak has been clipped at 60% of its maximum current. FIG. 12A further shows the energy/Hz diagram for this clipped sinusoidal waveform, which demonstrates that the energy is delivered in a very narrow band around the target frequency. If human studies do prove that it is the peak current that is primarily responsible for pain, then a clipped sinusoidal waveform may deliver the maximum amount of energy in the desired frequency band and still minimize the peak current. Likewise, these sinusoidal waveform data support the application of the teachings of the present invention to design waveforms that will optimize the energy delivered in the desired frequency range.

As was shown in the previous section on applications for transthoracic defibrillation, a multiphasic truncated exponential waveform can be designed to deliver more energy in the desired frequency band than does a biphasic waveform, especially at longer durations. For the internal atrial defibrillation application with an implantable device, the waveform would need to be optimized with the additional constraint that the waveform be something that can be generated by an implantable sized device. In this application, the overall waveform duration would be increased by using a larger capacitance, which then translates into a longer time constant. The polarity of this long time constant truncated exponential waveform would then be switched back and forth at the desired frequency, to generate a multiphasic truncated exponential waveform. These waveforms would be very similar to those shown in the previous section, only the pulse duration would ideally be longer than the 20 msec duration shown. Experimental studies would be necessary to pick the optimal time constant of decay, the optimal pulse duration, and the optimal switching frequency for internal atrial defibrillation of humans. But animal studies have indicated that a higher optimal frequency exists for atrial defibrillation than for ventricular defibrillation.

Defibrillate With a Frequency That Will Not Stimulate Pain Receptors

There exists a second application of this invention to the problem of reducing the pain of atrial defibrillation. That is to defibrillate the atria with an un-optimal shock, that might require more energy to succeed than presently used waveforms, but that might also be less able to stimulate pain receptors than the currently used waveforms. The teachings of this invention are ideally suited for this application, for three reasons: 1) it has been shown that the ability to defibrillate the ventricles with sinusoidal waveforms is frequency dependent; 2) it has been shown that the perception and pain thresholds to electrical stimulation of skin and skeletal muscle with sinusoidal waveforms is frequency dependent; and 3) the diastolic pacing threshold and fibrillation threshold with sinusoidal waveforms have also been shown to be frequency dependent. From this previous experience (detailed below), I can reason that the ability to cause pain by an atrial defibrillation shock with sinusoidal or multiphasic waveforms will also prove to be frequency dependent. By designing a waveform in the frequency domain, to minimize the energy delivered at frequencies that cause pain, we can design a waveform that will defibrillate the atria and not cause pain. Since the energy requirements are so low for atrial defibrillation, it may be possible to find a shock that requires 2 or even many times the energy of the best biphasic waveform, but delivers this energy at a frequency that doesn't stimulate pain receptors. Such a shock might be better tolerated by patients.

1. Frequency Dependence to Defibrillation

In the two studies I did at UAB, I found that ventricular defibrillation efficacy with sinusoidal waveforms is a function of frequency for both 20 msec and 40 msec duration shocks (FIGS. 10A to 10J and 11A to 11J). This relationship shows that very low frequencies are not very good for defibrillation, and that as the frequency is increased, the efficacy gets better to a maximum efficacy around 75–100 Hz. Then, as the frequency is increased further, the efficacy goes down again. The ED50 current for defibrillation with a 300 Hz waveform is about 60% higher than that for the optimal frequency. If this 300 Hz waveform were less able to stimulate pain receptors, then increasing the delivered energy would not be a problem, since the electrical requirements for atrial defibrillation are so small.

2. Frequency Dependence to Cutaneous and Skeletal Muscle Stimulation

The curve relating the perception of cutaneous stimulation and pain by electrical stimulation with sinusoidal waveforms is also frequency dependent. The frequency dependence of these waveforms exhibits a similar relationship, increasing to an optimal frequency in the 50 to 100 Hz range, and then decreasing at higher frequencies. Electrical requirements for perception of a 300 Hz waveform are higher than for the optimal frequency. And a similar relationship is seen for perception of skeletal muscle stimulation with sinusoidal waveforms.

3. Frequency Dependence to Cardiac Pacing and Fibrillation Thresholds

Cardiac stimulation by sinusoidal waveforms has been shown to exhibit a frequency dependence, with a relationship that is very similar to these other curves, with decreasing efficacy at very low and high frequencies. Likewise, the fibrillation threshold to stimulation by sinusoidal waveforms has also been shown to exhibit a similar frequency dependence. Atrial defibrillation with a higher frequency waveform would have the additional advantage that it would be less likely to induce ventricular fibrillation than currently used waveforms.

It is likely that the pain threshold of atrial defibrillation with sinusoidal waveforms will exhibit a frequency dependence that is similar to all of these curves. If it does, then hypothetically a waveform of 300, 600, 1000 Hz, or even a higher frequency, might be able to defibrillate (although with more energy than the optimal waveform), but might not stimulate pain receptors as well as the optimal shocks. The duration of these waveforms can also be made longer, to reduce the required peak current, which may prove to be important in avoiding pain. Therefore, it is possible that a longer duration, higher frequency waveform might be able to defibrillate at 6 to 15 joules, but not be as painful as a 2 to 3 joule BTE waveform. Typical implantable ventricular defibrillators can deliver 25 to 30 joules, without being too large to implant. Therefore, the energy will not be the limiting factor here, as long as the energy is delivered in frequencies that will defibrillate the atria and not stimulate pain receptors.

In this application of the present invention, the energy is again delivered in a targeted frequency band, only now the target has moved to higher un-optimal frequencies. These previously published studies suggest that higher frequencies will not be as painful as frequencies around 100 Hz. And our data suggests that higher frequencies will require higher currents than the frequencies around 100 Hz. Therefore, the determining factor will be the relative slopes of these two curves. If the pain threshold curve and the defibrillation ED50 curve have the same slope, then there may be no advantage gained with the higher frequency shocks. However, if these two curves diverge at higher frequencies, then it will be possible to design a multiphasic waveform of three or more pulses whose energy is delivered at un-optimal frequencies, and which will cause less pain to the patient receiving the shock. In a similar manner to that discussed in more detail in the following section, it may also be possible to identify the frequency ranges that are stimulating the pain receptors, and filter these frequencies out of an effective waveform. Again the waveform will be optimized in the frequency domain, and then transformed back into the time domain.

C) Representative Applications of This Invention to Internal Ventricular Defibrillation One application of this invention to internal ventricular defibrillation will be very similar to the application discussed previously for external ventricular defibrillation. Although the patient impedance does not vary as widely with internal ventricular defibrillation as it does with external ventricular defibrillation, there is still a range of patient impedance which must be addressed. In addition, the time constant for the average impedance patient must be selected by choosing the optimal capacitance; and the optimal duration and switching frequency must be determined experimentally. Using the teachings of this invention, one could design a multiphasic truncated exponential waveform, that would deliver the maximum amount of energy in the desired frequency band. In response to a change in impedance, this method would keep the frequency of stimulation constant, or in the predetermined sequence if variable pulse durations are indicated (as was discussed previously in section A).

Another application of this invention to internal ventricular defibrillation would involve identifying frequency bands that are important to defibrillation and frequency bands that are not important to defibrillation. One could then design a filter, to delete the energy from the frequency bands that are not contributing to defibrillation, which will then allow a lower energy waveform with equivalent defibrillation efficacy. I predict, subject to experimental verification, that the very low and higher frequencies will not contribute to defibrillation efficacy. If this proves to be true, then energy in these frequencies can be filtered out of the output before applying the waveform to the patient.

D) Experimental Studies Supporting This Invention

Transthoracic Defibrillation

An animal study has been performed, comparing the ventricular defibrillation efficacy of the industry standard Edmark waveform, the BTE waveform of the Heartstream FORERUNNER® device, and a quadriphasic truncated exponential (QTE) waveform that has been designed based on the teachings of this invention. These three waveforms were tested for defibrillation efficacy at each of three impedance levels, chosen to simulate the average human impedance and two extremes. The waveforms shown in FIGS. 13A to 13I were tested in a canine model of transthoracic defibrillation. Parameters of the QTE waveform such as time constant, individual pulse duration, and overall pulse duration will need to be optimized in further animal studies, and may need to be further refined in tests in humans. However, this study points to some of the advantages of the present invention over the prior art. The data from the study, shown in Table 1 and in FIG. 13J, demonstrate the superior transthoracic defibrillation efficacy of the BTE waveform over the Edmark waveform across all simulated impedance levels studied ($p<0.0001$). In addition, the data shows that the new QTE waveform also exhibited superior defibrillation efficacy to the Edmark waveform, which was again evident across all simulated impedance levels studied ($p<0.0001$). Direct comparison of the BTE and QTE waveforms showed that overall there was no significant difference in defibrillation efficacy across the 5 energy-impedance combinations studied. However, at one combination (138Ω, 24 J), the QTE waveform was considered more effective then the BTE waveform (71% vs. 49%, $p=0.011$ (borderline significance)). A supplemental study was performed, to compare the BTE and QTE waveforms in simulated high impedance patients. This study found the QTE waveform mean ED50 peak current estimate was approximately 1 A lower than that observed with the BTE waveform ($p=0.0049$). The results of this study suggest that the QTE waveform is as effective as the BTE waveform in low and average impedance patients, and potentially more effective in high impedance patients. This is important clinically, as high impedance patients reportedly have poorer outcomes with present defibrillators. A QTE waveform, or similar multiphasic waveform depending on further studies, could easily be implemented in a clinically relevant device, since the circuit parameters such as capacitance and peak voltage would stay the same. The difference is that the output polarity would be switched three times, rather than once as with the BTE waveform. Another advantage to the QTE waveform is that the impedance compensation strategy is a passive strategy, and no patient electrical parameters need to be monitored during the shock discharge. This modification could potentially translate into smaller and less expensive defibrillators, which might be important in the development of automatic external defibrillators for the lay public use. Several public health organizations have advocated widespread dissemination of public access defibrillators in buildings and areas that experience large numbers of people. To achieve these goals, the defibrillators need to be easy to use, and less expensive than currently available models. This study has shown that a defibrillation waveform using the principles of this invention yields a waveform that is more effective than the prior art, and that can be generated with a simpler, and probably less expensive defibrillator.

TABLE 1

Measured electrical parameters (mean ± s.d.) from the primary portion of this study. For each class of waveform (Edmark, BTE, and QTE) three simulated impedance levels were studied (39, 85, and 138 Ω) at two different target energy levels (18 and 24 J).

| Waveform Ω–Energy(J) | Peak Current (A) | Peak Voltage (V) | Impedance (Ω) | Delivered Energy (J) | Percent Success * |
|---|---|---|---|---|---|
| Edmark | | | | | |
| 39 Ω–18 J | 13.9 ± 1.3 | 751 ± 6.6 | 54.3 ± 5.8 | 17.3 ± 1.6 | 31 |
| 85 Ω–18 J | 12.5 ± 1.0 | 683 ± 21.0 | 55.0 ± 5.4 | 18.0 ± 1.5 | 9 |
| 85 Ω–24 J | 14.0 ± 1.3 | 752 ± 15.1 | 54.2 ± 6.1 | 22.5 ± 2.2 | 27 |
| 138 Ω–18 J | 10.8 ± 1.0 | 598 ± 19.9 | 55.8 ± 6.2 | 18.4 ± 1.6 | 4 |
| 138 Ω–24 J | 12.7 ± 0.8 | 679 ± 18.0 | 53.7 ± 3.9 | 24.8 ± 1.5 | 20 |
| BTE | | | | | |
| 39 Ω–18 J | 13.1 ± 1.2 | 718 ± 10.9 | 54.8 ± 5.5 | 17.9 ± 0.7 | 47 |
| 85 Ω–18 J | 8.9 ± 0.8 | 511 ± 10.4 | 57.3 ± 5.9 | 18.0 ± 0.7 | 51 |
| 85 Ω–24 J | 10.6 ± 0.8 | 586 ± 10.0 | 55.0 ± 4.9 | 23.9 ± 0.9 | 69 |
| 138 Ω–18 J | 7.0 ± 0.7 | 405 ± 5.1 | 58.4 ± 6.2 | 17.7 ± 0.6 | 42 |
| 138 Ω–24 J | 8.3 ± 0.7 | 469 ± 7.9 | 56.5 ± 4.9 | 24.1 ± 1.0 | 49 |
| QTE | | | | | |
| 39 Ω–18 J | 13.0 ± 1.2 | 719 ± 10.3 | 55.6 ± 5.0 | 18.0 ± 0.7 | 51 |
| 85 Ω–18 J | 9.0 ± 0.8 | 509 ± 9.9 | 56.6 ± 5.5 | 18.1 ± 0.9 | 53 |
| 85 Ω–24 J | 10.5 ± 0.9 | 583 ± 8.8 | 55.3 ± 5.5 | 24.3 ± 0.9 | 78 |
| 138 Ω–18 J | 7.1 ± 0.7 | 406 ± 5.2 | 57.5 ± 6.1 | 17.8 ± 0.8 | 49 |
| 138 Ω–24 J | 8.3 ± 0.7 | 469 ± 9.1 | 56.2 ± 5.7 | 23.9 ± 0.9 | 71 |

* BTE and QTE success were > Edmark success across all treatments ($p < 0.0001$). BTE and QTE success were not different, except at 138 Ω–24 J ($p = 0.011$, see text).

FIG. 14 is a block diagram of a clinical device according to the invention. In this form, the invention comprises an apparatus for treating fibrillation or tachycardia. The invention includes a discharging energy source 141 for energy storage, such as a bank of capacitors, two patient electrodes 142 adapted to make electrical contact with a patient and a connecting mechanism forming an electrical circuit between the energy source and the electrodes and a controller. The connecting mechanism may be wires 143 from the energy storage connected via switches 144 which are connected to the patient electrodes 142 via patient cables 145. A controller 146 operates the connecting mechanism, such as by opening and closing switches 144, to deliver pulses of electrical energy from the energy source 141 to the patient electrodes 142. In accordance with one form of the invention, the pulses constitute a multiphasic waveform having three or more pulses optimized in the frequency domain. In accordance with another form of the invention, the controller 146 operates the connecting mechanism to deliver electrical energy from the energy source to the electrodes having a particular one of a plurality of waveforms (e.g., monophasic, biphasic and/or multiphasic), each of which is optimized in the frequency domain.

The invention also is embodied in a method of generating a waveform for treating fibrillation or tachycardia in a patient comprising the steps of:

discharging the energy source 141 across the patient electrodes 142 in contact with the patient (such as by closing switches 144) to deliver electrical energy from the energy source 141 to the electrodes 142; and optimizing the waveform in the frequency domain.

Internal Atrial and Ventricular defibrillation

FIG. 15I is a graph illustrating the mean ED50 peak current required for atrial defibrillation with biphasic and multiphasic waveforms with the same time constant and overall duration within the pairs as shown in FIGS. 15A to 15H. These data are from a study conducted in an ovine model of atrial defibrillation, with epicardial electrodes. FIG. 16 is a graph illustrating the mean ED50 peak current required for ventricular defibrillation with biphasic and multiphasic waveforms with the same time constant and overall duration within the pairs as shown in FIGS. 15A to 15H. The waveforms which yielded the data in FIGS. 15A to 15I are identical to the waveforms which yielded the data in FIG. 16. These graphs show the following. First, the biphasic waveform loses its efficacy for atrial defibrillation very dramatically, while it retains its efficacy for ventricular defibrillation as duration increases; which is a very important difference suggesting an inherent difference in the atrial and ventricular tissues. Second, the multiphasic waveform retains its efficacy for both atrial and ventricular defibrillation as duration increases. Third, longer duration multiphasic waveforms, with optimized switching frequencies in the frequency domain, allow a reduction in the peak current required for both atrial and ventricular defibrillation. Reducing the peak current required for atrial defibrillation of humans even more than shown here is possible after optimizing the frequency of stimulation and waveform duration; and this should yield a pain-free electrical therapy for atrial defibrillation.

SUMMARY OF EXPERIMENTAL DATA

Figure 13A:
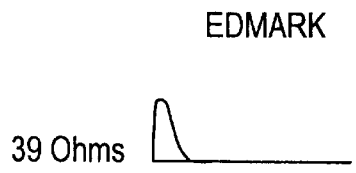
Figure 13D:
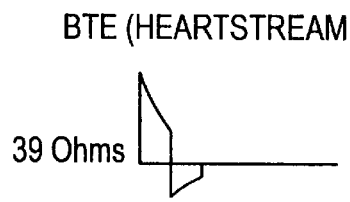
Figure 13G:
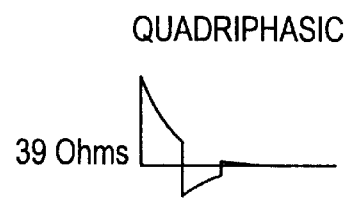
Figure 13B:
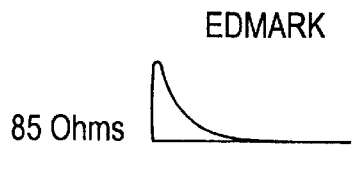
Figure 13E:
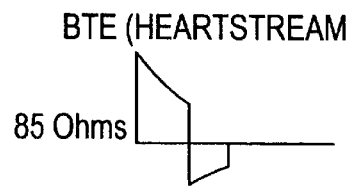
Figure 13H:
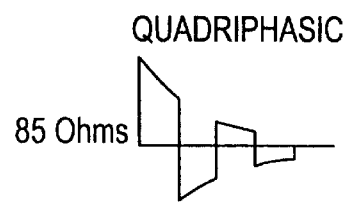
Figure 13C:
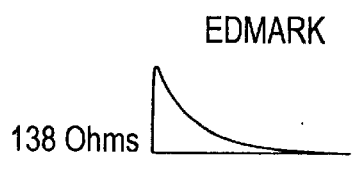
Figure 13F:
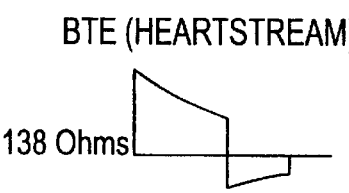
Figure 13I:
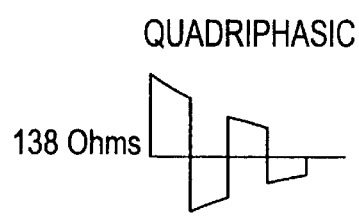

The application of this invention to ventricular defibrillation with external electrodes was the subject of a study summarized in FIGS. 13A and 13J that demonstrated that a multiphasic waveform showed a pronounced improvement over the Edmark waveform, and an improvement over the biphasic waveform of the Heartstream FORERUNNER® device in high impedance patients. Since patient impedance varies so much more with external defibrillation than it does with internal defibrillation, impedance compensation is very important with external defibrillators. My animal study suggests that a multiphasic waveform will out-perform the biphasic waveform in high impedance human patients. Advantages to the multiphasic waveform of the present invention over the present state of the art include: passive impedance compensation, not requiring any impedance measurements during the shock discharge; more effective in high impedance patients than the active impedance compensation strategy of the Heartstream FORERUNNER® device; and less energy left on the capacitors when the shock is finished, which energy needs to be dumped somewhere.

All these advantages translate into a smaller, less complicated, less expensive, more effective external defibrillator.

The application of this invention to atrial and ventricular defibrillation with internal electrodes was the subject of studies that were summarized in FIGS. 15A to 15I and 16. Our studies found that the multiphasic waveform retains its efficacy for atrial defibrillation as the duration is increased to 24 msec when the individual pulse durations were 6 msec for a switching frequency of 83 Hz. When the same waveforms were studied with internal ventricular defibrillation, the biphasic waveform retained its efficacy at longer durations, but even then the multiphasic waveform required less peak current than the biphasic waveform. Another study varying the switching frequency of multiphasic truncated exponential waveforms found that frequencies as high as 138 Hz required lower peak currents than did the 83 Hz waveform. Further studies are needed of even higher frequencies than 138 Hz for atrial defibrillation. In any case, the data to date suggests that the atria prefers higher frequencies of stimulation than do the ventricles. We expect that durations out to 50 or 100 msec will show a further reduction in the peak current required for atrial defibrillation. The Incontrol company reported that ⅓ of their patients could be taught to tolerate their 12 msec overall duration BTE shock; ⅓ of their patients wanted a sedative to take the edge off of the pain during a shock; and ⅓ of their patients wanted to be anesthetized before the shock was applied. If we assume that it is the peak current (or voltage) that directly relates to the pain associated with atrial defibrillation, and if the teachings of this invention can reduce this peak current (or voltage) required by 20%, that would likely be a significant improvement over the prior art. As that would probably mean that perhaps 50% of the patients could tolerate the treatment, rather than the ⅓ that currently can. However, if the present invention can reduce the peak current to about half of that which is required now, that we will have a waveform that can painlessly defibrillate the atria with internal electrodes.

If further experimental studies find that reducing the peak current is not sufficient to reduce the pain of atrial defibrillation, then it may be possible to define an unoptimal shock waveform, that requires 2 or 3 times as much energy as an optimal shock, but still doesn't cause pain. The reason for this is that there is a frequency dependence to pain from electrical stimulation. There is also a similar frequency dependence to the ability to defibrillate the atria. This suggests that a 400 to 600 Hz shock, which might require a lot more energy than an optimal BTE waveform, will be less able to stimulate the pain receptors and therefore, will cause less pain. Even higher frequencies, such as 1,000 to 2,000 Hz, will be even less able to stimulate the pain receptors but further studies will be necessary to confirm that the atria can be defibrillated with these frequencies. In any case, the waveforms will be optimized in the frequency domain, to maximize the energy delivered in beneficial frequency bands, and minimize the energy delivered in other frequency bands.

FIGS. 17A to 17F illustrate the importance of the phase angle of the Fourier transform in determining the efficacy for defibrillation of an electrical waveform. Two biphasic waveforms are shown in FIGS. 17A and 17B: FIG. 17A shows a 35 A $1^{st}$ phase amplitude and an 18 A $2^{nd}$ phase amplitude; FIG. 17B an 18 A $1^{st}$ phase amplitude and a 35 A $2^{nd}$ phase amplitude. All phase durations in both waveforms are 4 msec. FIGS. 17C and 17D show the amplitude of the Fourier transform for each waveform, while FIGS. 17E and 17F show the phase angle of the Fourier transform of each waveform. When the MU lab studied these waveforms in ventricular defibrillation of calves with external electrodes, the first was 75% successful, while the second was only 23% successful. Since the Fourier transform is a reversible transformation, all the information contained in the waveforms in the time domain is also present in the frequency domain representation. Since the graphs of the amplitude of the Fourier transform of these two waveforms is identical, then the difference in efficacy must be due to the differences in the graphs of the phase angle. The waveform is optimized in the frequency domain by selecting a waveform so that a dominant frequency of the Fourier transform of the waveform in the frequency domain is in a preselected range and selecting the optimal phase angle of the transform of the waveform in the frequency domain. In other words, the waveform designed in the frequency domain by selecting an energy distribution and a phase angle in the frequency domain and by generating a reverse Fourier transform to define the waveform in the time domain.

Figure 18A:
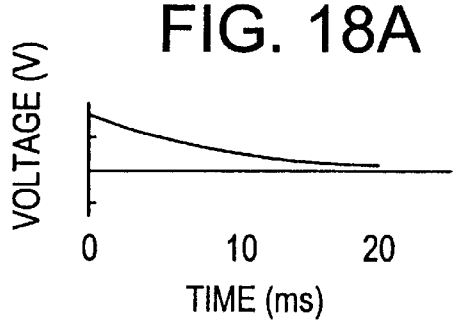
Figure 18B:
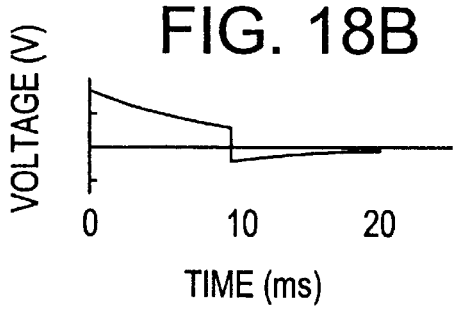
Figure 18C:
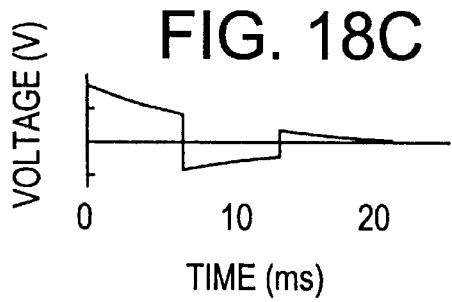
Figure 18D:
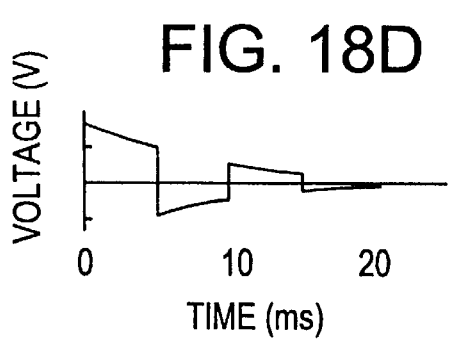
Figure 18E:
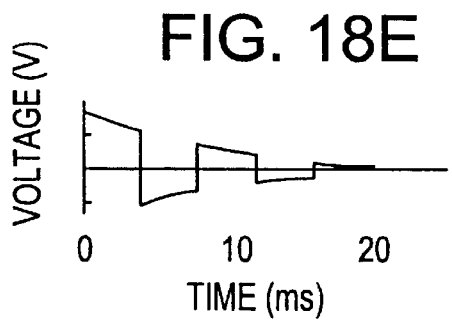
Figure 18F:
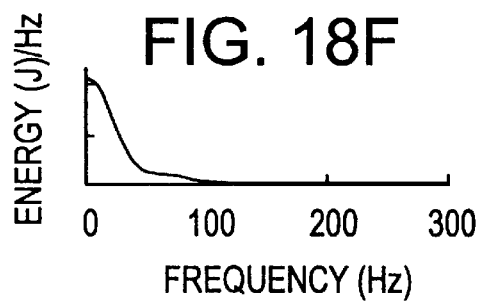
Figure 18G:
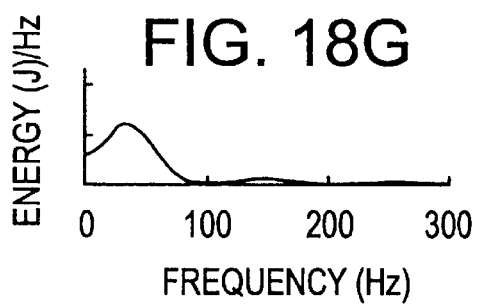
Figure 18H:
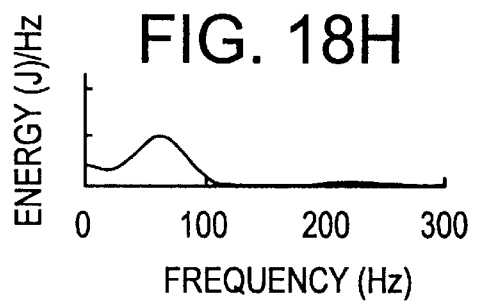
Figure 18I:
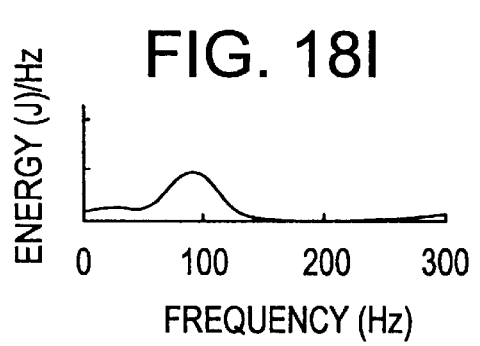
Figure 18J:
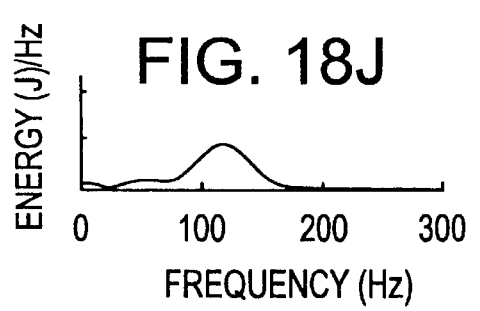

FIGS. 18A to 18J illustrate how the switching frequency of the truncated exponential waveform effects the dominant frequency lobe of the Fourier transform. All waveforms have the same duration and time constant of decay; and are shown in the time domain in the left column and in the frequency domain in the right column. The waveform of FIGS. 18A and 18F is monophasic, and the dominant frequency lobe is about 0 Hz. The waveform of 18B and 18G is biphasic, and the dominant frequency lobe is about 40 Hz. The Fourier transform of the triphasic waveform of FIGS. 18C and 18H has a dominant frequency of about 75 Hz. The dominant frequency of the quadriphasic waveform of FIGS. 18D and 18I is about 100 Hz. And the dominant frequency of the pentaphasic waveform of FIGS. 18E and 18J is about 120 Hz. By selecting the switching frequency, the dominant frequency lobe of the Fourier transform can be located at an optimal frequency.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. A method of generating a waveform for treating fibrillation or tachycardia in a patient comprising:

discharging an energy source across electrodes in contact with the patient to deliver electrical energy from the energy source to the electrodes having a multiphasic waveform containing three or more pulses; and optimizing the waveform in the frequency domain.

2. The method of claim 1 wherein the waveform is optimized in the frequency domain so that a dominant frequency of the waveform in the frequency domain is in the range of about 40–160 Hertz, or about 400 to 600 Hertz, or about 1,000 to 2,000 Hertz.

3. The method of claim 1 wherein the percentage of the energy of the waveform that is delivered in frequencies within the desired frequency range is greater than the percent of energy of the waveform outside the desired frequency range.

4. The method of claim 1 wherein the waveform has pulses having a fixed total duration of about 20 milliseconds or about 50–100 milliseconds.

5. The method of claim 1 wherein the controller delivers electrical energy from the energy source to the electrodes having a quadriphasic truncated exponential waveform containing four pulses optimized in the frequency domain.

6. The method of claim 1 wherein the waveform is optimized in the frequency domain so that a dominant frequency of the Fourier transform of the waveform in the frequency domain is selected to maximize efficacy.

7. The method of claim 1 wherein the waveform is optimized in the frequency domain by selecting a waveform so that a dominant frequency of the Fourier transform of the waveform in the frequency domain is in a preselected range and/or by selecting an optimal phase angle of the transform of the waveform in the frequency domain.

8. The method of claim 1 wherein the waveform is optimized in the frequency domain by selecting an energy distribution and a phase angle in the frequency domain and by generating a reverse Fourier transform to define the waveform in the time domain.

9. The method of claim 1, wherein the waveform is optimized in the frequency domain so that a dominant frequency of the Fourier transform of the waveform in the frequency domain is selected to minimize pain.

10. An apparatus for treating fibrillation or tachycardia comprising a pulse generator adapted to generate a multiphasic waveform containing three or more pulses optimized in the frequency domain.

11. The apparatus of claim 10 wherein the waveform is optimized in the frequency domain so that a dominant frequency of the Fourier transform of the waveform in the frequency domain is selected to maximize efficacy.

12. The apparatus of claim 10 wherein the waveform is optimized in the frequency domain by selecting a waveform so that a dominant frequency of the Fourier transform of the waveform in the frequency domain is in a preselected range and/or by selecting an optimal phase angle of the transform of the waveform in the frequency domain.

13. The apparatus of claim 10 wherein the waveform is optimized in the frequency domain by selecting an energy distribution and a phase angle in the frequency domain and by generating a reverse Fourier transform to define the waveform in the time domain.

14. The apparatus of claim 10 wherein the waveform is optimized in the frequency domain so that a dominant frequency of the waveform in the frequency domain is in the range of about 40–160 Hertz, or about 400 to 600 Hertz, or about 1,000 to 2,000 Hertz.

15. The apparatus of claim 10 wherein the percentage of energy of the waveform within the desired range is greater than the percent of energy of the waveform outside the desired range.

16. The apparatus of claim 10, wherein the waveform is optimized in the frequency domain so that a dominant frequency of the Fourier transform of the waveform in the frequency domain is selected to minimize pain.

17. An apparatus for treating fibrillation or tachycardia comprising:

a discharging energy source;

two electrodes adapted to make electrical contact with a patient;

a connecting mechanism forming an electrical circuit between the energy source and the electrodes; and a controller operating the connecting mechanism to deliver pulses of electrical energy from the energy source to the electrodes having a multiphasic waveform containing three or more pulses optimized in the frequency domain.

18. The apparatus of claim 17 wherein the waveform is optimized in the frequency domain so that a dominant frequency of the Fourier transform of the waveform in the frequency domain is selected to maximize efficacy.

19. The apparatus of claim 17 wherein the waveform is optimized in the frequency domain by selecting a waveform so that a dominant frequency of the Fourier transform of the waveform in the frequency domain is in a preselected range and/or by selecting an optimal phase angle of the transform of the waveform in the frequency domain.

20. The apparatus of claim 17 wherein the waveform is optimized in the frequency domain by selecting an energy distribution and a phase angle in the frequency domain and by generating a reverse Fourier transform to define the waveform in the time domain.

21. The apparatus of claim 17 wherein the waveform is optimized in the frequency domain so that a dominant frequency of the waveform in the frequency domain is in the range of about 40–160 Hertz, or about 400 to 600 Hertz, or about 1,000 to 2,000 Hertz.

22. The apparatus of claim 21 wherein the percentage of energy of the waveform within the desired range is greater than the percent of energy of the waveform outside the desired range.

23. The apparatus of claim 17 wherein at least one of the electrodes is adapted to electrically contact a patient's skin or the patients ventricular for ventricular defibrillation or ventricular cardioversion (to treat tachycardia) and wherein the waveform is optimized in the frequency domain so that a dominant frequency of the waveform in the frequency domain is about 100 Hertz.

24. The apparatus of claim 23 wherein the pulses have a total fixed duration of about 20 milliseconds.

25. The apparatus of claim 17 wherein the electrodes are adapted to electrically contact a patient's skin or the patient's atria for atrial defibrillation or atrial cardioversion (to treat tachycardia) and wherein the waveform is optimized in the frequency domain so that a dominant frequency of the waveform in the frequency domain is about 125 Hertz.

26. The apparatus of claim 25 wherein the pulses have a total fixed duration of about 50–100 milliseconds.

27. The apparatus of claim 17 wherein the controller delivers electrical energy from the energy source to the electrodes having a quadriphasic truncated exponential waveform containing four pulses optimized in the frequency domain.

28. The apparatus of claim 17 wherein each of the pulses has the same fixed pulse duration.

29. The apparatus of claim 28 wherein the pulses have about a 5 millisecond duration.

30. The apparatus of claim 27 wherein the pulses have a fixed total duration.

31. The apparatus of claim 30 wherein the fixed total duration is about 20 milliseconds.

32. The apparatus of claim 30 wherein the fixed total duration is about 50–100 milliseconds.

33. The apparatus of claim 17 wherein the pulses are discontinued when their magnitude falls below a preset voltage.

34. The apparatus of claim 33 wherein the preset voltage is about 25% of the initial pulse voltage.

35. The apparatus of claim 17 wherein the pulses are discontinued when the capacitive charge of the discharging energy source falls below a preset voltage.

36. The apparatus of claim 35 wherein the preset voltage is about 25% of the initial capacitive charge.

37. The apparatus of claim 17 wherein the pulses have a variable pulse duration.

38. The apparatus of claim 37 wherein the pulses have successively decreasing durations.

39. The apparatus of claim 38 wherein the pulses have durations of 6 milliseconds, 5.5 milliseconds, 4.5 milliseconds and 4 milliseconds.

40. The apparatus of claim 17 wherein the waveform is optimized in the frequency domain so that a dominant frequency of the Fourier transform of the waveform in the frequency domain is selected to minimize pain.

41. An apparatus comprising:

a discharging energy source;

two electrodes adapted to make electrical contact with a patient;

a connecting mechanism forming an electrical circuit between the energy source and the electrodes; and a controller operating the connecting mechanism to deliver electrical energy from the energy source to the electrodes having a particular one of a plurality of waveforms, each of which is optimized in the frequency domain according to a parameter and wherein the controller selects the particular waveform based on the parameter so that the selected particular waveform is optimized in the frequency domain to have a dominant frequency in a preset range.

42. The apparatus of claim 41 wherein the parameter is an impedance between the electrodes, a frequency of fibrillation, or an amplitude of fibrillation.

43. The apparatus of claim 41 wherein the waveform is optimized in the frequency domain so that a dominant frequency of the waveform in the frequency domain is in the range of about 40–160 Hertz, or about 400 to 600 Hertz, or about 1,000 to 2,000 Hertz.

44. The apparatus of claim 41 wherein the controller delivers electrical energy from the energy source to the electrodes having a quadriphasic truncated exponential waveform containing four pulses optimized in the frequency domain.

* * * * *